United States Patent
Kazlauskas

(10) Patent No.: US 11,464,773 B2
(45) Date of Patent: *Oct. 11, 2022

(54) NUTLIN-3A FOR TREATMENT OF PROLIFERATIVE VITREORETINOPATHY

(71) Applicant: The Schepens Eye Research Institute, Inc., Boston, MA (US)

(72) Inventor: Andrius Kazlauskas, Winchester, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/379,717

(22) Filed: Apr. 9, 2019

(65) Prior Publication Data

US 2020/0138806 A1 May 7, 2020

Related U.S. Application Data

(63) Continuation of application No. 15/476,265, filed on Mar. 31, 2017, now abandoned, which is a continuation of application No. 14/622,169, filed as application No. PCT/US2013/055432 on Aug. 16, 2013, now Pat. No. 9,623,024.

(60) Provisional application No. 61/683,887, filed on Aug. 16, 2012.

(51) Int. Cl.
| | |
|---|---|
| *A61K 31/496* | (2006.01) |
| *A61P 27/02* | (2006.01) |
| *C07D 403/06* | (2006.01) |
| *C12N 15/113* | (2010.01) |

(52) U.S. Cl.
CPC ........ *A61K 31/496* (2013.01); *C12N 15/1135* (2013.01); *C12N 15/1138* (2013.01); *C12N 2310/14* (2013.01); *C12N 2320/30* (2013.01)

(58) Field of Classification Search
CPC ... A61P 27/02; A61K 31/496; C12N 15/1135; C12N 15/1138; C12N 2310/14; C12N 2320/30; C07D 403/06
See application file for complete search history.

(56) References Cited

U.S. PATENT DOCUMENTS

| 9,623,024 B2 | 4/2017 | Kazlauskas |
| 2009/0298785 A1 | 12/2009 | Dyer et al. |
| 2010/0239499 A1 | 9/2010 | Drenser |
| 2013/0190387 A1 | 7/2013 | Feinstein |
| 2015/0224088 A1 | 8/2015 | Sarkar et al. |
| 2015/0313893 A1 | 11/2015 | Kazlauskas |
| 2018/0064708 A1 | 3/2018 | Kazlauskas |

FOREIGN PATENT DOCUMENTS

| WO | 2011056961 A2 | 5/2011 |
| WO | 2012047587 A2 | 4/2012 |

OTHER PUBLICATIONS

Andrews, et al., "Platelet-Derived Growth Factor Plays a Key Role in Proliferative Vitreoretinopathy", Investigative Ophthalmology & Visual Science, Oct. 1999, 40(11):2683-2689.
Asaria, et al., "Adjuvant 5-fluorouracil and Heparin Prevents Proliferative Vitreoretinopathy Results From a Randomized, Double-Blind, Controlled Clinical Trial", Ophthalmology, 2001, 108(7):1179-1183.
Baudouin, et al., "Immunohistologic Study of Epiretinal Membranes in Proliferative Vitreoretinopathy", American Journal of Ophthalmology, 1990, 110(6):593-598.
Brennan, et al., "Targeting the p53 Pathway in Retinoblastoma with Subconjunctival Nutlin-3a", Cancer Research, 2011, 71:4205-4213.
Cahn, et al., "Errata: Specification of Molecular Chirality", Angewandte Chemie International Edition, 1966, 5(5):511.
Cahn, et al., "Specification of Configuration about Quadricovalent Asymmetric Atoms", Journal of the Chemical Society, 1951, 612-622.
Cahn, et al., "Specification of Molecular Chirality", Angewandte Chemie International Edition, 1966, 5(4):385-415.
Cahn, et al., "The Specification of Asymmetric Configuration in Organic Chemistry", Experientia, 1956, 12:81-124.
Cahn, "An Introduction to the Sequence Rule: A System for the Specification of Absolute Configuration", Journal of Chemical Education, 41(3):116-125, 1964.
Campochiaro, et al., "Pathogenic Mechanisms in Proliferative Vitreoretinopathy", Archives of Ophthalmology, 1997, 115(2):237-241.
Charteris, "Growth factors in proliferative vitreoretinopathy", British Journal of Ophthalmology, Feb. 1998, 82(2):106.
Cui, et al., "PDGF Receptors are Activated in Human Epiretinal Membranes", Experimental Eye Research, Mar. 2009, 88(3):438-444.
Database GenBank, "Canis familiaris p53 protein (p53) mRNA, complete cds", GenBank Accession No. AF060514.1, May 22, 1998, 1 page.
Database GenBank, "double minute 2 protein [Equus caballus]", GenBank Accession No. AAF28866.1, Apr. 18, 2000, 1 page.
Database GenBank, "E3 ubiquitin-protein ligase Mdm2 [Felis catus]", NCBI Reference Sequence: NP_001009346.1, Jul. 15, 2012, 2 pages.
Database GenBank, "E3 ubiquitin-protein ligase Mdm2 [Rattus norvegicus]", NCBI Reference Sequence: NP_001101569.1, May 27, 2012, 2 pages.
Database GenBank, "E3 ubiquitin-protein ligase Mdm2 isoform a [*Homo sapiens*]", GenBank Accession No. NP_002383.2, Jul. 22, 2012, 3 pages.
Database GenBank, "Equus caballus p53 gene exons 5 to 9", GenBank Accession No. X91793.1, Nov. 14, 2006, 2 pages.
Database GenBank, "MDM2 [Canis lupus familiaris]", GenBank Accession No. AAG42840.1, Jan. 2, 2001, 1 page.
Database GenBank, "mdm2 [Mus musculus]", GenBank Accession No. AAB09030.1, Sep. 28, 1996, 2 pages.

(Continued)

*Primary Examiner* — Brenda L Coleman
(74) *Attorney, Agent, or Firm* — Fish & Richardson P.C.

(57) ABSTRACT

The invention provides compositions and methods for treatment of proliferative vitreoretinopathy.

17 Claims, 14 Drawing Sheets

Specification includes a Sequence Listing.

(56) References Cited

OTHER PUBLICATIONS

Database GenBank, "RecName: Full=Cellular tumor antigen p53; AltName: Full=Tumor suppressor p53", GenBank Accession No. P41685.1, Jul. 11, 2012, 7 pages.

Database GenBank, "Tumor protein p53 [Rattus norvegicus]", GenBank Accession No. AAH81788.2, Mar. 18, 2009, 2 pages.

Database GenBank, "tumor suppressor p53 [Mus musculus]", GenBank Accession No. AAC05704.1, Mar. 16, 1998, 1 page.

Database GenBank, "tumor suppressor protein p53 [Homo sapiens]", GenBank Accession No. AAD28535.1, Mar. 28, 2002, 2 pages.

Druker, et al., "Efficacy and Safety of a Specific Inhibitor of the BCR-ABL Tyrosine Kinase in Chronic Myeloid Leukemia", The New England Journal of Medicine, Apr. 5, 2001, 344(14):1031-1037.

Fastenberg, et al., "The Role of Cellular Proliferation in an Experimental Model of Massive Periretinal Proliferation", American Journal of Ophthalmology, May 1982, 93(5):565-572.

Giono, et al., "Mdm2 is Required for Inhibition of Cdk2 Activity by p21, Thereby Contributing to p53-Dependent Cell Cycle Arrest", Molecular and Cellular Biology, Jun. 2007, 27(11):4166-4178.

Girard, et al., "Clinical risk factors for proliferative vitreoretinopathy after retinal detachment surgery", Retina, 1994, 14(5):417-24.

Gottlieb, et al., "Cross-talk between Akt, p53 and MDM2: Possible Implications for the Regulation of Apoptosis", Oncogene, 2002, 21:1299-1303.

Haimann, et al., "Epidemiology of retinal detachment", Archives of Ophthalmology, Feb. 1982, 100(2):289-292.

Hainaut, et al., "p53 and Human Cancer: The First Ten Thousand Mutations", Advances in Cancer Research, 2000, 77:81-137.

Han, "Proliferative Vitreoretinopathy", Albert Jakobiec's Principles and Practice of Ophthalmology. Philadelphia, PA: Elsevier Saunders, 2008, Chapter 183, pp. 2315-2324.

Haupt, et al., "Mdm2 Promotes the Rapid Degradation of p53", Nature, 1997, 387:296-299.

Ikuno, et al., "An In Vivo Gene Therapy Approach for Experimental Proliferative Vitreoretinopathy Using the Truncated Platelet-Derived Growth Factor α Receptor", Investigative Ophthalmology & Visual Science, 2002, 43(7):2406-2411.

Ikuno, et al., "Attenuation of Experimental Proliferative Vitreoretinopathy by Inhibiting the Platelet-Derived Growth Factor Receptor", Investigative Ophthalmology & Visual Science, Sep. 2000, 41(10):3107-3116.

Kumar, et al., "Role of daunorubicin in inhibiting proliferative vitreoretinopathy after retinal detachment surgery", Clinical and Experimental Ophthalmology, Oct. 4, 2002, 30(5):348-351.

Lei, et al., "A Novel Function of p53", The American Journal of Pathology, Sep. 2012, 181(3):866-874.

Lei, et al., "A Potential Role for PDGF-C in Experimental and Clinical Proliferative Vitreoretinopathy", Investigative Ophthalmology & Visual Science, 2007, 4:2335-2342.

Lei, et al., "Growth Factors Outside of the PDGF Family Drive Experimental PVR", Investigative Ophthalmology & Visual Science, 2009, 50(7):3394-3403.

Lei, et al., "Growth Factors Outside of the Platelet-Derived Growth Factor (PDGF) Family Employ Reactive Oxygen Species/Src Family Kinases to Activate PDGF Receptor α and Thereby Promote Proliferation and Survival of Cells", Journal of Biological Chemistry, 2009, 284(10):6329-6336.

Lei, et al., "N-Acetycysteine Retinal Detachment in an Experimental Model of Proliferative Vitreoretinopathy", The American Journal of Pathology, Jul. 2010, 177(1):132-140.

Lei, et al., "Pathological Signaling via Platelet-Derived Growth Factor Receptor α Involves Chronic Activation of Akt and Suppression of p53", Molecular and Cellular Biology, May 2011, 31(9):1788-1799.

Lei, et al., "Recent Developments in our Understanding of how Platelet Derived Growth Factor (PDGF) and its Receptors Contribute to Proliferative Vitreoretinopathya", Experimental Eye Research, 2010, 90(3):376-381.

Levine, et al., "The First 30 Years of p53: Growing Ever More Complex", Nature Reviews Cancer, Oct. 2009, 9(10):749-758.

Levine, et al., "The p53 Tumour Supressor Gene", Nature, Jun. 6, 1991, 351:453-456.

Loewer, et al., "Basal Dynamics of P53 Reveals Transcriptionally Attenuated Pulses in Cycling Cells", Cell, Jul. 9, 2010, 142(1):89-100.

Lotsova, et al., "Down Regulation of Fibronectin Gene Expression by the p53 Tumor Suppressor Protein", Cell Growth & Differentiation, 1996, 7:629-634.

Mendrysa, et al., "mdm2 is Critical for Inhibition of p53 during Lymphopoiesis and the Response to Ionizing Irradiation", Molecular and Cellular Biology, Jan. 2003, 23(2):462-473.

Mendrysa, "Tumor Suppression and Normal Aging in Mice with Constitutively High P53 Activity", Genes & Development, 2006, 20:16-21.

Michels, et al., "Retinal Detachment", Baltimore: The C. V. Mosby Company, 1990, 669-706.

Mietz, et al., "Onset and recurrence of proliferative vitreoretinopathy in various vitreoretinal diseases", British Journal of Ophthalmology, Oct. 1995, 79(10):874-877.

Morales, et al., "Collagen Gel Contraction by ARPE-19 Cells is Mediated by a FAK-Src Dependent Pathway", Experimental Eye Research, 2007, 85:790-798.

Morales, et al., "FAK Activation and the Role of Epithelial Membrane Protein 2 (EMP2) in Collagen Gel Contraction", Investigative Ophthalmology & Visual Science, 2009, 50(1):462-469.

Morales, "Functional Consequences of Interactions between FAK and Epithelial Membrane Protein 2 (EMP2)", Investigative Ophthalmology & Visual Science, Oct. 2009, 50(10):4949-4956.

Morales, et al., "Rewiring Integrin-Mediated Signaling and Cellular Response with the Peripheral Myelin Protein 22 and Epithelial Membrane Protein 2 Components of the Tetraspan Web", Investigative Ophthalmology & Visual Science, Jul. 2011, 52(8):5465-5472.

Nagasaki, et al., "Comparative Study of Clinical Factors that Predispose Patients to Proliferative Vitreoretinopathy in Aphakia", Retina, 1991, 11(2):204-207.

Ofir-Rosenfield, et al., "Mdm2 regulates p53 mRNA translation through inhibitory interactions with ribosomal protein L26", Molecular Cell, Oct. 24, 2008, 32(2):180-189.

Ogawara, et al., "Atk Enhances Mdm2-mediated Ubiquitination and Degradation of P53", Journal of Biological Chemistry, Jun. 14, 2002, 277(24):21843-21850.

Pennock, et al., "A Novel Strategy to Develop Therapeutic Approaches to Prevent Proliferative Vitreoretinopathy", The American Journal of Pathology, Dec. 2011, 179(6):2931-2940.

Perez, et al., "Clinical Risk Factors for Proliferative Vitreoretinopathy after Retinal Detachment Surgery", Arch. Soc. Esp. Oftalmol., 2000, 75(11):741-750.

Prives, "Signaling to p53: Breaking the MDM2-p53 Circuit", Cell, Oct. 2, 1998, 95(1):5-8.

Qiu, et al., "Id1-Induced Inhibition of P53 Facilitates Endothelial Cell Migration and Tube Formation by Regulating the Expression of Beta1-Integrin", Molecular and Cellular Biochemistry, 2011, 357:125-133.

Robbins, et al., "Platelet-Derived Growth Factor Ligands and Receptors Immunolocalized in Proliferative Retinal Diseases", Investigative Ophthalmology & Visual Science, 1994, 35(10):3649-3663.

Rodriguez De La Rua, et al., "Interaction between Surgical Procedure for Repairing Retinal Detachment and Clinical Risk Factors for Proliferative Vitreoretinopathy", Current Eye Research, 2005, 30(2):147-153.

Rozenkranz, et al., "Identification of the Receptor-associated Signalling Enzymes that are Required for Platelet derived Growth Factor-AA-dependent Chemotaxis and DNA Synthesis", Journal of Biological Chemistry, May 7, 1999, 274(40):28335-28343.

(56) References Cited

OTHER PUBLICATIONS

Sasaki, et al., "Regulation of the MDM2-p53 Pathway and Tumor Growth by PICT1 via Nucleolar RPL11", Nature Medicine, Jul. 11, 2011, 17(8):944-951.
Schiff, et al., "Safety and Efficacy Assessment of Chimeric Ribozyme to Proliferating Cell Nuclear Antigen to Prevent Recurrence of Proliferative Vitreoretinopathy", Archives of Ophthalmology, 2007, 125(9):1161-1167.
Secchiero, et al., "Recent advances in the therapeutic perspectives of Nutlin-3", Current Pharmaceutical Design, 2011, 17(6):569-577.
Telander, "Epithelial Membrane Protein-2 (EMP2) and Experimental Proliferative Vitreoretinopathy (PVR)", Curyent Eye Research, Jan. 31, 2011, 36(6):546-552.
Tseng, et al., "Prevalence and Risk Factors for Proliferative Vitreoretinopathy in Eyes with Rhegmatogenous Retinal Detachment but no Previous Vitreoretinal Surgery", American Journal of Ophthalmology, 2004, 137(6):1105-1115.
Vassilev, et al., "In Vivo Activation of the p53 Pathway by Small-Molevule Antagonists of MDM2", Science, Feb. 6, 2004, 303:844-848.
Vinores, "Ultrastructural and Electron-Immunocytochimical Characterization of Cells in Epithelial Membranes", Investigative Ophthalmology & Visual Science, 1990, 31(1):14-28.
Wiedemann, et al., "Adjunctive Daunorubicin in the Treatment of Proliferative Vitreoretinopathy: Results of a Multicenter Clinical Trial. Daunomycin Study Group", American Journal of Ophthalmology, 1998, 126(4):550-559.
Wilkes, et al., "The incidence of retinal detachment in Rochester, Minnesota, 1970-1978", American Journal of Ophthalmology, Nov. 1982, 94(5):670-673.
Wong, et al., "Induction of Proliferative Vitreoretinopathy by a Unique Line of Human Retinal Pigment Epithelial Cells", Canadian Journal of Ophthalmology, 2002, 37:211-220.
Yoshino, et al., "Comparative Study of Clinical Factors Predisposing Patients to Proliferative Vitreoretinopathy", Retina, 1989, 9(2):97-100.
Zhou, "HER-2/Neu Induces p53 Ubiquination via ATK-Mediated MDM2 Phosphorylation", Nature Cell Biology, Nov. 2001, 3:973-982.
International Preliminary Report on Patentability in International Appln. No. PCT/US2013/055432, dated Feb. 17, 2015, 13 pages.
International Search Report and Written Opinion in International Appln. No. PCT/US2013/055432, dated Jan. 3, 2014, 16 pages.

FIG. 9A
FIG. 9B
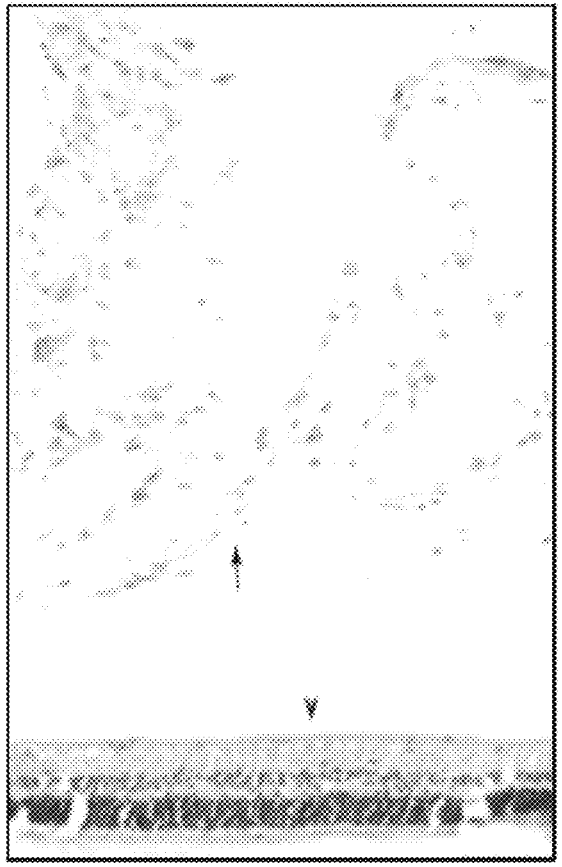
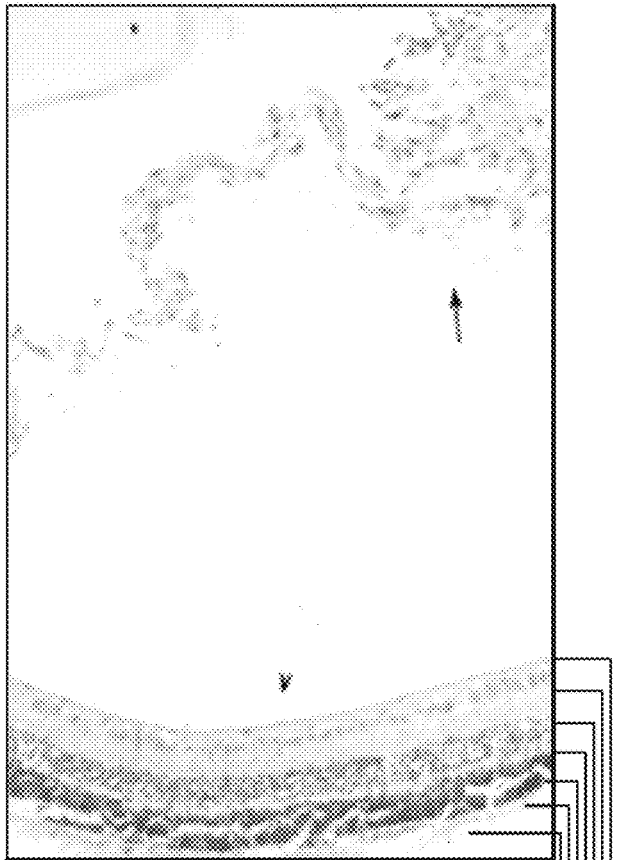
outer segments of rods and cones
rods and cones
outer nuclear layer
outer plexiform layer
inner nuclear layer
inner plexiform layer
ganglion cell

SEQUENCE LISTING

```
<160> NUMBER OF SEQ ID NOS: 6

<210> SEQ ID NO 1
<211> LENGTH: 393
<212> TYPE: PRT
<213> ORGANISM: Homo sapiens

<400> SEQUENCE: 1

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125
```

```
Ala Leu Asn Lys Met Phe Cys Gln Leu Ala Lys Thr Cys Pro Val Gln
        130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Lys Glu Asn
            275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 2
<211> LENGTH: 497
<212> TYPE: PRT
<213> ORGANISM: Homo sapiens

<400> SEQUENCE: 2

Met Val Arg Ser Arg Gln Met Cys Asn Thr Asn Met Ser Val Pro Thr
1               5                   10                  15

Asp Gly Ala Val Thr Thr Ser Gln Ile Pro Ala Ser Glu Gln Glu Thr
            20                  25                  30

Leu Val Arg Pro Lys Pro Leu Leu Leu Lys Leu Leu Lys Ser Val Gly
        35                  40                  45

Ala Gln Lys Asp Thr Tyr Thr Met Lys Glu Val Leu Phe Tyr Leu Gly
    50                  55                  60

Gln Tyr Ile Met Thr Lys Arg Leu Tyr Asp Glu Lys Gln Gln His Ile
65                  70                  75                  80

Val Tyr Cys Ser Asn Asp Leu Leu Gly Asp Leu Phe Gly Val Pro Ser
                85                  90                  95

Phe Ser Val Lys Glu His Arg Lys Ile Tyr Thr Met Ile Tyr Arg Asn
```

```
                100             105              110
Leu Val Val Asn Gln Gln Glu Ser Ser Asp Ser Gly Thr Ser Val
            115             120             125
Ser Glu Asn Arg Cys His Leu Glu Gly Gly Ser Asp Gln Lys Asp Leu
130             135             140
Val Gln Glu Leu Gln Glu Lys Pro Ser Ser Ser His Leu Val Ser
145             150             155             160
Arg Pro Ser Thr Ser Ser Arg Arg Ala Ile Ser Glu Thr Glu Glu
            165             170             175
Asn Ser Asp Glu Leu Ser Gly Glu Arg Gln Arg Lys Arg His Lys Ser
            180             185             190
Asp Ser Ile Ser Leu Ser Phe Asp Glu Ser Leu Ala Leu Cys Val Ile
            195             200             205
Arg Glu Ile Cys Cys Glu Arg Ser Ser Ser Glu Ser Thr Gly Thr
            210             215             220
Pro Ser Asn Pro Asp Leu Asp Ala Gly Val Ser Glu His Ser Gly Asp
225             230             235             240
Trp Leu Asp Gln Asp Ser Val Ser Asp Gln Phe Ser Val Glu Phe Glu
            245             250             255
Val Glu Ser Leu Asp Ser Glu Asp Tyr Ser Leu Ser Glu Glu Gly Gln
            260             265             270
Glu Leu Ser Asp Glu Asp Asp Glu Val Tyr Gln Val Thr Val Tyr Gln
            275             280             285
Ala Gly Glu Ser Asp Thr Asp Ser Phe Glu Glu Asp Pro Glu Ile Ser
            290             295             300
Leu Ala Asp Tyr Trp Lys Cys Thr Ser Cys Asn Glu Met Asn Pro Pro
305             310             315             320
Leu Pro Ser His Cys Asn Arg Cys Trp Ala Leu Arg Glu Asn Trp Leu
            325             330             335
Pro Glu Asp Lys Gly Lys Asp Lys Gly Glu Ile Ser Glu Lys Ala Lys
            340             345             350
Leu Glu Asn Ser Thr Gln Ala Glu Glu Gly Phe Asp Val Pro Asp Cys
            355             360             365
Lys Lys Thr Ile Val Asn Asp Ser Arg Glu Ser Cys Val Glu Glu Asn
370             375             380
Asp Asp Lys Ile Thr Gln Ala Ser Gln Ser Gln Glu Ser Glu Asp Tyr
385             390             395             400
Ser Gln Pro Ser Thr Ser Ser Ile Ile Tyr Ser Ser Gln Glu Asp
            405             410             415
Val Lys Glu Phe Glu Arg Glu Glu Thr Gln Asp Lys Glu Glu Ser Val
            420             425             430
Glu Ser Ser Leu Pro Leu Asn Ala Ile Glu Pro Cys Val Ile Cys Gln
            435             440             445
Gly Arg Pro Lys Asn Gly Cys Ile Val His Gly Lys Thr Gly His Leu
            450             455             460
Met Ala Cys Phe Thr Cys Ala Lys Lys Leu Lys Lys Arg Asn Lys Pro
465             470             475             480
Cys Pro Val Cys Arg Gln Pro Ile Gln Met Ile Val Leu Thr Tyr Phe
            485             490             495
Pro

<210> SEQ ID NO 3
<211> LENGTH: 15
```

```
<212> TYPE: PRT
<213> ORGANISM: Artificial Sequence
<220> FEATURE:
<223> OTHER INFORMATION: Synthesized phospho-peptide
<220> FEATURE:
<221> NAME/KEY: MISC_FEATURE
<222> LOCATION: (8)..(8)
<223> OTHER INFORMATION: Phosphorylation

<400> SEQUENCE: 3

Lys Gln Ala Asp Thr Thr Gln Tyr Val Pro Met Leu Asp Met Lys
1               5                   10                  15

<210> SEQ ID NO 4
<211> LENGTH: 21
<212> TYPE: DNA
<213> ORGANISM: Artificial Sequence
<220> FEATURE:
<223> OTHER INFORMATION: Synthesized oligo

<400> SEQUENCE: 4
gccagctctt attaccctct a                                                21

<210> SEQ ID NO 5
<211> LENGTH: 21
<212> TYPE: DNA
<213> ORGANISM: Artificial Sequence
<220> FEATURE:
<223> OTHER INFORMATION: Synthesized oligo

<400> SEQUENCE: 5
cgggcgtaaa cgcttcgaga t                                                21

<210> SEQ ID NO 6
<211> LENGTH: 21
<212> TYPE: DNA
<213> ORGANISM: Artificial Sequence
<220> FEATURE:
<223> OTHER INFORMATION: Synthesized oligo

<400> SEQUENCE: 6
acaacagcca caacgtctat a                                                21
```

NUTLIN-3A FOR TREATMENT OF PROLIFERATIVE VITREORETINOPATHY

RELATED APPLICATIONS

This Application is a Continuation of application Ser. No. 15/476,265 filed on Mar. 31, 2017. application Ser. No. 15/476,265, now abandoned, is a Continuation of application Ser. No. 14/622,169 filed on Feb. 13, 2015, now U.S. Pat. No. 9,623,024, issued Apr. 18, 2017. Application PCT/US2013/055432 claims the benefit of U.S. Provisional Application 61/683,887 filed on Aug. 16, 2012. The entire contents of these applications are incorporated herein by reference in their entirety.

STATEMENT AS TO FEDERALLY SPONSORED RESEARCH

This invention was funded in part by the U.S. Government under grant number EY012509, awarded by the National Eye Institute. The Government has certain rights in the invention.

INCORPORATION BY REFERENCE OF SEQUENCE LISTING

The contents of the text file named "36770-527001WO_ST25.txt", which was created on Aug. 16, 2013 and is 8.7 KB, are hereby incorporated by reference in its entirety.

FIELD OF THE INVENTION

This invention relates generally to the field of ophthalmology.

BACKGROUND OF THE INVENTION

Proliferative vitreoretinopathy (PVR) is a blinding disease that afflicts 5-11% of patients that undergo surgery to correct a rhegmatogenous retinal detachment. There are between 1,700 and 3,700 cases of PVR annually in the US. The current treatment for PVR is repeat surgery, which is anatomically successful in only 60-80% of cases, and the procedure carries the risk of recurrence. Prior to the invention described herein, efforts to identify non-surgical, i.e., pharmacological, approaches to treat PVR have not been successful. Thus, there is a pressing need for new therapy options for individuals who are afflicted by this blinding disease.

SUMMARY OF THE INVENTION

The invention is based on the surprising discovery that preventing the reduction of intra-ocular p53 by administering the small molecule, Nutlin-3, prevents retinal detachment, the most sight-threatening component of proliferative vitreoretinopathy. The invention provides compositions and methods for inhibiting or reducing the severity of proliferative vitreoretinopathy (PVR) in a subject.

Accordingly, a method for inhibiting or reducing the severity of PVR is carried out by identifying a subject suffering from or at risk of developing PVR, and administering a composition comprising an agent that inhibits or reduces an intra-ocular reduction of the level of p53 associated with PVR. The subject is preferably a mammal in need of such treatment, e.g., a subject that has been diagnosed with PVR or a predisposition thereto. For example, the level of p53 associated with PVR is reduced by 10%, 25%, 50%, or reduced by 2-fold, 10-fold, or more, and administration of compositions of the present invention prevents, inhibits, or reduces the reduction of p53 levels associated with PVR. Alternatively, the administration of the compositions of the present invention causes a 10%, 20%, 30%, 40%, or 50% increase in p53 levels compared to the p53 levels associated with PVR or the p53 levels prior to treatment, or a 2-fold, 3-fold, 4-fold, or 5-fold increase in p53 levels compared to the levels associated with PVR or the p53 levels prior to treatment. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. For example, the mammal is a performance mammal, such as a racehorse or racedog (e.g., greyhound). Preferably, the mammal is a human.

In some cases, the subject suffering from or at risk of developing PVR has undergone rhegmatogenous retinal detachment surgery. A subject that is suffering from PVR is identified by presenting with any PVR indication. PVR indications include the appearance of vitreous haze and retinal pigment epithelial (RPE) cells in the vitreous humor, a wrinkling of the edges of a retinal tear or the inner retinal surface, or by the presence of retinal membranes. A subject that is at risk of developing PVR is identified by presenting with any PVR risk factor. Risk factors for PVR include age, aphakia/pseudophakia, high levels of vitreous proteins, duration of retinal detachment before corrective surgery, the size of the retinal hole or tear, intra-ocular inflammation, vitreous hemorrhage, intraocular pressure, extended retinal detachments, reinterventions, scleral surgery, and trauma or injury to the eye. Other subjects at risk for developing PVR are individuals that engage in activities with increased risk for trauma or injury to or in the proximity of the eye. Examples of such subjects include, but are not limited to, boxers, wrestlers, military personnel, young males. Preferably, the subject has not been diagnosed with cancer, such as an ocular cancer. Preferably, the subject has not been diagnosed with a retinoblastoma. The subject is greater than 3 months old, 6 months old, 9 months old, 12 months old, 18 months old, 24 months old, 30 months old, or 36 months old. Preferably, the subject is an adolescent or an adult.

Preferably, the agent that inhibits or reduces an intra-ocular reduction of the level of p53 associated with PVR is an agent that prevents, inhibits, or reduces p53 from interacting with human double min 2 (Hdm2). Thus, the agent increases the level of p53. In some cases, the reduction of the level of p53 is a platelet-derived growth factor receptor α (PDGFRα)-mediated reduction. For example, the agent that inhibits the intra-ocular reduction of the level of p53 is a polynucleotide, a polypeptide, an antibody, or a small molecule. The upper molecular weight limit for a small molecule is approximately 800 Daltons which allows for the possibility to rapidly diffuse across cell membranes so that the molecule can reach intracellular sites of action. Nutlins, a family of cis-imidazoline analogues, are small-molecule double min 2 antagonists that inhibit the interaction or association between p53 and Hdm2. Preferably, the small molecule comprises Nutlin-3a (RG7112/RO5045337). Preferably, the agent is a functional analog of Nutlin-3a, in which the analog prevents, inhibits, or reduces p53 from interacting or associating (e.g., binding) with Hdm2. Methods for identifying such functional analogs are also described herein.

The structure of Nutlin-3a is reproduced below:

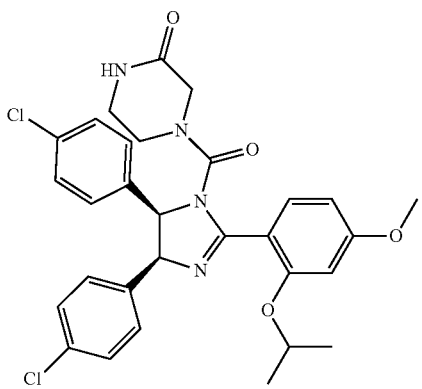 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

Nutlin-3a is administered at a concentration ranging from 0.1 μM to 500 μM, e.g., between 0.5 μM and 400 μM; between 1.0 μM and 300 μM; between 2.0 μM and 200 μM; between 5 μM and 175 μM; between 10 μM and 150 μM; between 20 μM and 125 μM; between 30 μM and 100 μM; or between 50 μM and 75 μM. Preferably, Nutlin-3a is administered at a concentration ranging from 2 to 50 μM. Preferably, Nutlin-3a is administered at a concentration of 200 μM at a dose of 0.1 ml/day, or scaled-up to an amount appropriate for human therapy.

Nutlin-3a is present in the compositions of the present invention at a concentration range of 0.1-10%, with preferred ranges between 1-5% and 2-2.5% (mg/ml). Exemplary liquid formulations for eye drops contain 2-2.5% (mg/ml) of the composition. Preferred formulations are in the form of a solid, a paste, an ointment, a gel, a liquid, an aerosol, a mist, a polymer, a film, an emulsion, or a suspension. The formulations are administered intravitreally or subconjunctivally.

The composition is administered every 96 hours, every 72 hours, every 48 hours, every 24 hours, every 12 hours, every 6 hours, every 3 hours, or every 1 hour. The composition is administered for a duration of 1 day, 2 days, 3 days, 5 days, 7 days, 10 days, 14 days, 20 days, 30 days, 60 days, 90 days, 120 days, 180 days or 365 days. For example, Nutlin-3a is administered intravitreally or subconjunctivally once per day for 7 days. Preferably, the administration is a local administration.

In a preferred method, the administration is intravitreal injection. Preferably, multiple intravitreal injections are administered to the subject over a period of at least 7 days, at least 14 days, at least 28 days. The multiple injections can be every day, every other day, every three days, every four days, every five days, every six days, or weekly for the duration of the treatment. Preferably, for each intravitreal injection, Nutlin-3a is administered at a concentration ranging from 2 to 50 μM.

In another preferred method, the administration is subconjunctival. For subconjunctival administration, a single administration is preferred, wherein the Nutlin-3a is at a concentration ranging from 2 to 50 μM, or preferably at a higher concentration than given over multiple injections, for example, ranging from 10 to 50 μM, 20 to 50 μM, 30 to 50 μM, or 40 to 50 μM. Preferably, the Nutlin-3a administered in a formulation suitable for sustained-release or slow-release of the active ingredient, such that Nutlin-3a is disseminated to or throughout the retina and/or proximal ocular tissues over time, for example, over at least one week, two weeks, three weeks, one month, or two months. Suitable formulations for a single administration include, but are not limited to, membranes, gels, creams, wafers, sponges, or degradable pellets.

The invention provides a composition comprising an agent that inhibits or reduces an intra-ocular reduction of the level of p53 associated with PVR, and/or prevents p53 from interacting or associating with human double min 2 (Hdm2). The composition is used for inhibiting or reducing the severity of proliferative vitreoretinopathy (PVR) in a subject suffering from or at risk of developing PVR. The intra-ocular reduction of the p53 level is mediated by platelet-derived growth factor receptor α (PDGFRα). The agent is a polynucleotide, a polypeptide, an antibody, or a small molecule, e.g., Nutlin-3a (RG7112/RO5045337) or an analog thereof. Nutlin-3a, or analogs thereof, is administered at a concentration of 0.1 μM, 0.5 μM, 1.0 μM, 2.0 μM, 5 μM, 10 μM, 20 μM, 30 μM, or 50 μM. Nutlin-3a, or analog thereof, is present in the composition at a concentration of 0.1-10% (mg/ml). The composition further comprises a pharmaceutically acceptable carrier. In some preferred embodiments, the composition is a solid, a paste, an ointment, a gel, a liquid, an aerosol, a mist, a polymer, a film, an emulsion, or a suspension.

Also within the invention is a pharmaceutical composition comprising a Nutlin-3a compound, or an analog thereof, and a pharmaceutically acceptable carrier and/or ophthalmic excipient. The pharmaceutical composition comprising a Nutlin-3a compound, or analog thereof, and a pharmaceutically acceptable carrier and/or an ophthalmic excipient is for use for inhibiting or reducing the severity of proliferative vitreoretinopathy (PVR).

Exemplary pharmaceutically acceptable carrier include a compound selected from the group consisting of a physiological acceptable salt, poloxamer analogs with carbopol, carbopol/hydroxypropyl methyl cellulose (HPMC), carbopol-methyl cellulose, carboxymethylcellulose (CMC), hyaluronic acid, cyclodextrin, and petroleum.

All compounds of the invention are purified and/or isolated. Specifically, as used herein, an "isolated" or "purified" small molecule (e.g., Nutlin-3a or a functional analog or variant thereof), nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

An "isolated nucleic acid" is a nucleic acid, the structure of which is not identical to that of any naturally occurring nucleic acid, or to that of any fragment of a naturally occurring genomic nucleic acid spanning more than three separate genes. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybridgene, i.e., a gene encoding a fusion protein. Isolated nucleic acid molecules according to the present invention further include molecules produced synthetically, as well as any nucleic acids that have been altered chemically and/or that have modified backbones. Isolated nucleic acid molecules also include messenger ribonucleic acid (mRNA) molecules.

Although the phrase "nucleic acid molecule" primarily refers to the physical nucleic acid and the phrase "nucleic acid sequence" refers to the linear list of nucleotides of the nucleic acid molecule, the two phrases can be used interchangeably.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to prevent PVR in a mammal. Ultimately, the attending physician or veterinarian decides the appropriate amount and dosage regimen.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1A is a photograph of a western blot showing the impact of Nutlin-3a on RV-mediated signaling events. Primary rabbit conjunctival fibroblasts (RCFs) were pre-treated with either Nutlin-3a (10 µM), or vehicle for 30 min and then exposed to either RV (diluted 1:3 in Dulbecco's Modified Eagle Medium (DMEM)), or DMEM for 2 hr. The resulting cell lysates were subjected to western blot analysis using the indicated antibodies. The numbers are a ratio of p-PDGFRα/PDGFRα, p-Akt/Akt or p53/RasGAP (Ras GTPase) activating protein. This data presented is representative of three independent experiments. FIG. 1B is a bar chart showing the impact of Nutlin-3a on RV-mediated contraction. RCFs were subjected to the collagen contraction assay as described above. Nutlin-3a (10 µM) or vehicle was included as indicated. The data were subjected to a paired t test; "*" denoted a statistically significant difference.

FIG. 2A is a dot plot illustrating the impact of Nutlin-3a on experimental PVR. RCFs were used to induce PVR as described below. The indicated rabbits received no additional injections (none) or 0.1 cc injections of either vehicle, or Nutlin-3a (20 µM) on day 0, 2 and 4. The data were subjected to an unpaired t test or one way Analysis of Variance (ANOVA) test; "*" denoted a statistically significant difference. FIG. 2B is a series of photographs showing that Nutlin-3a enhanced expression of p53 in epiretinal membranes. At the end of the experiment (day 28), the eyes were enucleated, and paraffin sections of whole eyes were subjected to p53 immunohistochemistry. The arrows point to the epiretinal membrane (the arrowheads denote the retina and the brown color indicates p53). The left and right panels are from a Nutlin-3a injected animal, whereas the middle panel is from a rabbit treated with vehicle. The left and middle panels were stained with the p53 antibody, whereas the right panel was stained with non-immune IgG. The scale bar is 50 µm.

FIG. 3A is a photograph of a western blot showing the knockdown RCFs. Lentiviruses were used to stably express short hairpin ribonucleic acids (shRNAs) directed against green fluorescent protein (GFP), PDGFRα, or p53 in primary RCFs. The resulting cell lysates were subjected to western blot analysis using the indicated antibodies. The signal intensity was quantified and expressed as a ratio of the loading control (RasGAP). The data presented are representative of two independent experiments. FIG. 3B is a photograph of a western blot showing the expression of PDGFRα potentiated RV-mediated suppression of p53. The cells described in panel A were left resting or exposed to vitreous (diluted 1:3 in DMEM) from normal rabbits (RV) for 2 hr, lysed and total cell lysates were subjected to western blot analysis with the indicated antibodies. The signal intensity was quantified and the data presented are representative of three independent experiments. The data were subjected to a paired t test; "*" denoted a statistically significant difference. FIG. 3C is a bar chart showing RV induced contraction of RCF-loaded collagen gels, which required PDGFRα-mediated suppression of p53. The cells described in panel A were subjected to a collagen contraction assay. RV (diluted 1:3 in DMEM) was added on top of the gels on day 0 and the replenished every 24 hr; the experiments was terminated on day 3. The panel below the bar graph shows photographs of representative gels. The data in the bar graph are triplicates within a single experiment. The data were subjected to a paired t test; "*" denoted a statistically significant difference. The data presented are representative of 3 independent experiments.

FIG. 5A is a bar chart showing the results of RCFs (sh GFP, sh PDGFRα, sh PDGFRα/sh p53, and sh p53) seeded into a 24-well plate at a density of $5 \times 10^4$ cells/well in DMEM+10% fetal bovine serum (FBS). After 6 hours the cells had attached, the medium was changed to either 0.5 ml DMEM, or rabbit vitreous (diluted 1:3 in DMEM). The media were replaced every day. The cells were counted with a hemocytometer on day 3. The mean +/−standard deviation of three independent experiments is shown; * denotes P<0.05 using a paired t-test. FIG. 5B is a bar chart showing the results of RCFs described in A seeded into 60 mm dishes at a density of 100,000 cells/dish in DMEM+10% FBS. After 6 hours the cells had attached, the medium was changed to either 3 ml DMEM, or rabbit vitreous (diluted 1:3 in DMEM). The media were replaced every day. On day 3, the cells were stained with fluorescein isothiocyanate (FITC)-conjugated annexin V and propidium iodide (PI) in an apoptosis assay kit by following the manufacturer's instructions. Cells that were stained with annexin V and/or PI were detected and quantified by flow cytometry in Coulter Beckman XL (Coulter C.). The mean+/−standard deviation of three independent experiments is shown; * denotes P<0.05 using a paired t-test. FIG. 5C is a bar chart showing the results of RCFs described in A seeded into a 12-well plate at a density of 10,000 cells/well in DMEM+10% FBS. After 6 hours the cells had attached, the medium was changed to either 1 ml DMEM, or rabbit vitreous (diluted 1:3 in DMEM). The media were replaced every day. On Day 3, the β-galactosidase activity was measured as outlined in the manufacturer's instructions. Both stained and unstained cells were counted and photographed under an inverted microscope. The mean+/−standard deviation of three independent experiments is shown; * denotes P<0.05 using a paired t-test. The scale bar is 50 μm.

FIG. 7A is a photograph of a western blot showing the impact of Nutlin-3a on HV-mediated signaling events. Methods were the same as FIG. 3A, but the RPE cells from a human patient epiretinal membrane were used in place of RCF, and HV (a pool of vitreous from 5 PVR patients diluted 1:3 in DMEM) was used in place of RV. The data presented are representative of three independent experiments. FIG. 7B is a bar chart showing the impact of Nutlin-3a on HV-mediated contraction. This experiments were the same as FIG. 3B with the modification noted in FIG. 7A. The data were subjected to a paired t test. "*" denoted a statistically significant difference. The data shown are representative of three independent experiments.

FIGS. 8A-8B include a series of photographs showing the minimum effective dose and maximum tolerated dose of Nutlin-3a. FIG. 8A is a series of photomicrographs of western blots showing RCFs pretreated with the indicated concentrations of Nutlin-3a for 30 min, and then exposed to RV (diluted 1:3 in DMEM) for 2 hours. Cells were lysed and resulting lysates were subjected to western blot analysis using the indicated antibodies. The data shown are representative of three independent experiments. FIG. 8B is a series of photographs showing RCFs grown to near confluence in DMEM+10% FBS, the medium was replaced with DMEM+5% FBS+the indicated concentration of Nutlin-3a. The medium was replaced every 24 hours, and the photographs were taken on day 3. The data shown are representative of two independent experiments. The scale bar is 50 μm.

FIGS. 9A-9B include a series of photographs showing epiretinal membranes from rabbits subjected to the PVR protocol. Rabbits that underwent a gas vitrectomy were intravitreally injected with the indicated concentration of Nutlin-3a on day 0, 2 and 4. The rabbits underwent a fundus examination on day 1, 3, 5, 7 and 14. Following the last fundus exam rabbits were euthanized, eyes were enucleated and fixed in 10% formalin. Sections were prepared, stained with hematoxylin and eosin, and then photographed. Representative photos of a Nutlin-3a (FIG. 9A) and vehicle (FIG. 9B) injected eye are presented. Arrowheads and arrows point to the retina and epiretinal membrane, respectively; scale bar: 50 μm. The lack of the retinal pigment epithelial cell layer is an artifact related to processing of the tissue.

FIG. 11A is a photograph showing western blot analysis of knockdown RCFs. Lentiviruses were used to stably express shRNAs directed against GFP, PDGFRα, or p53 in primary RCFs. The resulting cell lysates were subjected to western blot analysis using the indicated antibodies. The signal intensity was quantified and expressed as a ratio of the loading control (RasGAP). The data presented are representative of two independent experiments. FIG. 11B is a photograph of a western blot showing that expression of PDGFRα potentiated RV-mediated suppression of p53. The cells described in panel A were left resting or exposed to vitreous (diluted 1:3 in DMEM) from normal rabbits (RV) for 2 hours, lysed and total cell lysates were subjected to western blot analysis with the indicated antibodies. The signal intensity was quantified and the data presented are representative of three independent experiments. FIG. 11C is a bar chart showing RV induced contraction of RCF-loaded collagen gels, which required PDGFRα-mediated suppression of p53. The cells (50,000 cells/ml) described in panel A were subjected to a collagen contraction assay. RV (diluted 1:3 in DMEM) was added on top of the gels on day 0 and the replenished every 24 hours; the experiments were terminated on day 3. The panel below the bar graph shows photographs of representative gels; the data presented are representative of 3 independent experiments. The data were subjected to a paired t test; "*" denoted a statistically significant difference.

FIG. 12A is a section of rat colon cancer that serves as that negative control for FIG. 12B.

DETAILED DESCRIPTION

Figure 1A:
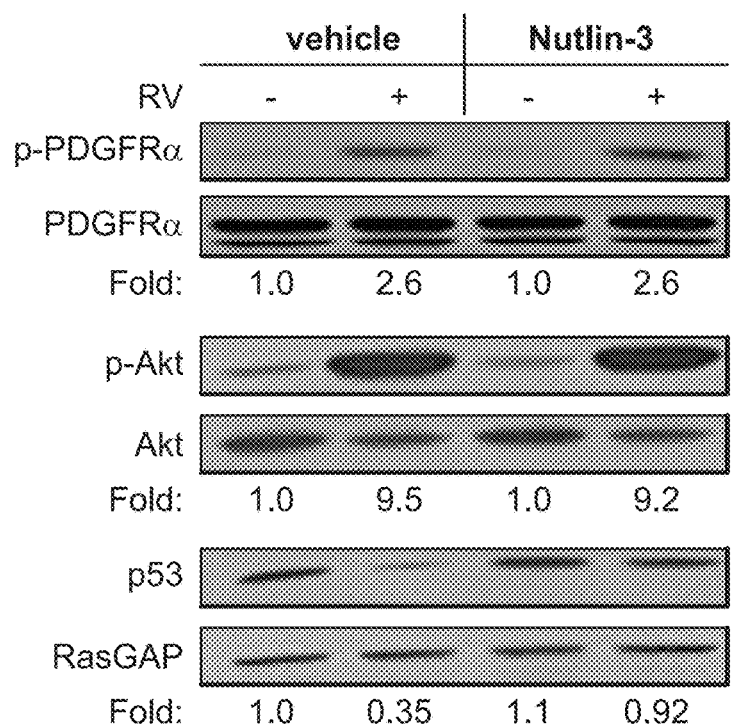
FIGS. 1A-1B include a photomicrograph of a western blot and a bar chart demonstrating that Nutlin-3a prevented both the rabbit vitreous humor (RV)-induced decline in the level of p53 and contraction.

Proliferative vitreoretinopathy is a blinding disease that afflicts 5-11% of patients that undergo surgery to correct a rhegmatogenous retinal detachment (Han D: Proliferative vitreoretinopathy. Edited by Albert D, J W. M, DT. A, BA. B. Philadelphia, Elsevier Saunders, 2008, pp. 2315-2324). There are between 1,700-3,700 cases of PVR in the US annually (Wilkes S R et al., 1982 Am J Ophthalmol, 94:670-673; Haimann M H et al., 1982 Arch Ophthalmol, 100:289-292). The current treatment for PVR is repeat surgery to remove the epiretinal membrane that is causing retinal detachment, and to reattach the detached retina (Charteris D G, 1998 Br J Ophthalmol, 82:106), which is anatomically successful in only 60-80% of cases (Michels R G, Wilkinson C P, Rice T A: Retinal Detachment. Edited by St. Louis, Mosby, 1990, p. pp. 669-706; Mietz H and Heimann K, 1995 Br J Ophthalmol, 79:874-8775). Moreover, the procedure carries the risk of recurrence (Girard P et al., 1994 Retina, 14:417-424; Lleo Perez A et al., 2000 Arch Soc Esp Oftalmol, 75:741-750; Nagasaki H et al., 1991 Retina, 11:204-207; Rodriguez de la Rua E et al., 2005 Curr Eye Res, 30:147-153; Tseng W et al., 2004 Am J Ophthalmol, 137:1105-1115; Yoshino Y et al., 1989 Retina, 9:97-100). Prior to the invention described herein, efforts to identify non-surgical, i.e., pharmacological, approaches to treat PVR were not successful (Wiedemann P et al., 1998 Am J Ophthalmol, 126:550-559; Asaria R H et al., 2001 Ophthalmology, 108:1179-1183; Schiff W M et al., 2007 Arch Ophthalmol, 125:1161-1167).

Nutlin-3a was first identified as a potent and selective small molecule inhibitor of the p53-MDM2 interaction. Subsequent studies showed that Nutlin-3a administration in vitro caused p53 stabilization and activation of the p53-pathway. Researchers have investigated the effects of Nutlin-3a administration to the eye, specifically in the context of a therapeutic strategy for treating retinoblastoma (Brennan et al., 2011 Cancer Res, 71(12): 4205-13). Retinoblastoma is a malignant tumor of the retina and it is estimated that up to 40% of retinoblastomas are hereditary. Retinoblastoma is a childhood cancer, and usually diagnosed in very young children between 12 months and 24 months of age. Because retinoblastomas retain wild-type p53 (instead, having a mutated RB1 gene that drives tumorigenesis), administration of Nutlin-3a may be useful as a cancer therapeutic by inducing effective p53-mediated apoptosis, senescence, or growth arrest in the tumor cells.

The data described herein demonstrate the surprising results that Nutlin-3a administration inhibited or reduced proliferative vitreoretinopathy and retinal detachment. These results are particularly intriguing, even in light of Brennan et al., because PVR and retinoblastoma are distinct ocular conditions. First, the etiologies of PVR and retinoblastoma are completely different—retinoblastoma is the uncontrolled growth and division of cells driven most often by mutations in the Rb1 (retinoblastoma) gene, while PVR is caused by a spontaneous event occurring after injury, trauma, or surgical procedure. Second, Nutlin-3a was a known p53 activator, and thus, the anti-tumorigenic effects in a wild-type p53 retaining cancer, such as retinoblastoma, were well known in the cancer field. However, unlike in cancers, the role of p53 and/or MDM2 has never been identified or implicated, prior to the invention, in a non-cancer setting, e.g., the development or mechanisms of PVR or retinal detachment. And finally, the patient populations affected by retinoblastoma and PVR are also entirely distinct. Retinoblastoma can develop in utero, and is usually diagnosed between 12 and 24 months of age. Moreover, many retinoblastoma patients inherited the disease. In contrast, PVR is associated with retinal detachment, which is a spontaneous event occurring after injury, trauma, or surgical procedure. PVR and retinal detachment often occur in the elderly (e.g., greater than 65 years of age), very near-sighted individuals, or individuals with a family history of retinal detachment. Thus, the patients affected by PVR are typically older than 12 or 24 months, and/or have suffered from a previous injury, trauma or surgical procedure to or near the proximity of the eye.

Proliferative Vitreoretinopathy

PVR is a blinding disease associated with rhegmatogenous retinal detachment, for which there is currently no satisfactory treatment. The term "proliferation" in "PVR" refers to the proliferation of retinal pigment epithelial and glial cells, while the terms "vitreo" and "retinopathy" identify the tissues which are affected, namely the vitreous humor (or simply vitreous) and the retina. Specifically, PVR is a disease that develops as a complication, secondary to rhegmatogenous retinal detachment. PVR occurs in about 8-10% of patients undergoing primary retinal detachment surgery, and can prevent the successful surgical repair of rhegmatogenous retinal detachment. Prior to the invention described herein, there were no prophylactic/preventative options available to patients that were at risk of PVR, e.g., those patients that had undergone retinal surgery.

The full-thickness retinal break (e.g., tears and holes) that is quintessential to rhegmatogenous retinal detachment results in exposure of cells to vitreous, a rich source of growth factors and cytokines (Oh K, Hartnett M, Landers I M: Pathogenic mechanisms of retinal detachment. Edited by Ryan S. Philadelphia, Elsevier Mosby, 2006). The accumulation of fluid in the sub-retinal space, along with the tractional force of the vitreous on the retina results in rhegmatogenous retinal detachment. Specifically, the RPE cells migrate into vitreous, proliferate, and synthesize extracellular matrix proteins (Han D: Proliferative vitreoretinopathy. Edited by Albert D, J W. M, DT. A, BA. B. Philadelphia, Elsevier Saunders, 2008, pp. 2315-2324). The cytokines present in the vitreous humor trigger the ability of the RPE to proliferate and migrate. This series of events culminates in the formation of a retina-associated membrane, which contracts and thereby causes retinal detachment and vision loss (Campochiaro P: The pathogenesis of proliferative vitreoretinopathy. Edited by Ryan S. Philadelphia, Elsevier Mosby, 2006).

While cells (retinal pigment epithelial, glial, fibroblasts, etc. (Campochiaro P A, 1997 Arch Ophthalmol, 115:237-241; Baudouin C et al., 1990 Am J Ophthalmol, 110:593-598; Vinores S A et al., 1990 Invest Ophthalmol Vis Sci, 31:14-28) in PVR membranes express a plethora of cell surface receptors, the PDGF receptor α is essential for experimental PVR, and is associated with clinical PVR (Andrews A et al., 1999 Invest Ophthalmol Vis Sci, 40:2683-2689; Robbins S G et al., 1994 Invest Ophthalmol Vis Sci, 35 No 10:3649-3663; Cui J et al., 2009 Exp Eye Res, 88:438-444). The surprisingly prominent role of PDGFRα in PVR is related to the fact that it can be engaged by a wide spectrum of vitreal agents, which activate the receptor indirectly and thereby trigger a signature set of signaling events that includes suppression of p53 (Lei H et al., 2009 J Biol Chem, 284:6329-6336; Lei H et al., 2009 Invest Ophthalmol Vis Sci, 50:3394-3403; Lei H et al., 2011 Mol Cell Biol, 31:1788-1799).

Predisposing factors for postoperative PVR are preoperative PVR, aphakia, high levels of vitreous proteins, duration of retinal detachment before corrective surgery, the size of the retinal hole or tear, intra-ocular inflammation, vitreous hemorrhage, vitreous liquidity, and trauma or injury to the eye. As described in Rodriguez de la Rua E et al., 2005 Curr Eye Res, 30:147-153, incorporated herein by reference, the risk for PVR was higher in patients >70 years, with intraocular pressure lower than 14 (OR: 3.84; CI 95%: 2.04-7.30), in retinal breaks larger than "1 clock hour" (OR: 2.54; CI: 1.28-5.05), extended retinal detachments (OR: 4.01; CI: 1.98-8.10), and reinterventions (OR: 1.55; CI: 1.14-9.22). Scleral surgery also was a risk factor for PVR (OR: 3.89; CI: 2.12-7.14) and aphakia/pseudophakia when scleral surgery is performed (OR: 3.33; CI: 1.54-7.22). In particular, some subjects that have undergone ocular surgeries, such as surgery to correct retinal detachments, are at increased risk for developing PVR.

The Interaction of P53 and Nutlin-3a

Various forms of cellular stress increase expression and activate p53, a tetrameric transcription factor, and thereby trigger the p53 pathway, which leads to cell cycle arrest, apoptosis and/or senescence (Levine A J et al., 2009 Nat Rev Cancer, 9:749-758). The finding that p53 and/or the p53 pathway is mutated in approximately 50% of solid tumors (Hainaut P and Hollstein M, 2000 Adv Cancer Res, 77:81-137) has lead to the development of pharmacological agents that stimulate the p53 pathway. For instance, the small molecule Nutlin-3a activates the p53 pathway by preventing p53 from interacting with Mdm2/Hdm2 (murine double min 2, also called Hdm2 in humans) (Vassilev L T et al., 2004 Science, 303:844-848), which reduces the level of p53 by a variety of mechanisms (Prives C, 1998 Cell, 95:5-8; Ofir-Rosenfeld Y et al., 2008 Mol Cell, 32:180-189; Sasaki M et al., 2011 Nat Med, 17:944-951).

The amino acid sequence of human p53 (Genbank Accession No. AAD28535.1) is as follows (SEQ ID NO: 1):

MEEPQSDPSVEPPLSQETFSDLWKLLPENNVLSPLPSQAMDDLMLSPDDIE

QWFTEDPGPDEAPRMPEAAPRVAPAPAAPTPAAPAPAPSWPLSSSVPSQKT

YQGSYGFRLGFLHSGTAKSVTCTYSPALNKMFCQLAKTCPVQLWVDSTPPP

GTRVRAMAIYKQSQHMTEVVRRCPHHERCSDSDGLAPPQHLIRVEGNLRVE

YLDDRNTFRHSVVVPYEPPEVGSDCTTIHYNYMCNSSCMGGMNRRPILTII

TLEDSSGNLLGRNSFEVRVCACPGRDRRTEKENLRKKGEPHHELPPGSTKR

ALPNNTSSSPQPKKKPLDGEYFTLQIRGRERFEMFRELNEALELKDAQAGK

EPGGSRAHSSHLKSKKGQSTSRHKKLMFKTEGPDSD

Orthologs for human p53 can be readily identified and are known in the art, for example, mouse (Genbank Accession No. AAC05704), rat (Genbank Accession No. AAH81788), cat (Genbank Accession No. P41685), dog (Genbank Accession No. AF060514) and horse (Genbank Accession No. X91793). Other isoforms and transcriptional variants of p53 are also known in the art.

The amino acid sequence of human double min 2 (Hdm2) (Genbank Accession No. NP_002383) is as follows (SEQ ID NO: 2):

MVRSRQMCNTNMSVPTDGAVTTSQIPASEQETLVRPKPLLLKLLKSVGAQK

DTYTMKEVLFYLGQYIMTKRLYDEKQQHIVYCSNDLLGDLFGVPSFSVKEH

RKIYTMIYRNLVVVNQQESSDSGTSVSENRCHLEGGSDQKDLVQELQEEKP

SSSHLVSRPSTSSRRRAISETEENSDELSGERQRKRHKSDSISLSFDESLA

LCVIREICCERSSSSESTGTPSNPDLDAGVSEHSGDWLDQDSVSDQFSVEF

EVESLDSEDYSLSEEGQELSDEDDEVYQVTVYQAGESDTDSFEEDPEISLA

DYWKCTSCNEMNPPLPSHCNRCWALRENWLPEDKGKDKGEISEKAKLENST

QAEEGFDVPDCKKTIVNDSRESCVEENDDKITQASQSQESEDYSQPSTSSS

IIYSSQEDVKEFEREETQDKEESVESSLPLNAIEPCVICQGRPKNGCIVHG

KTGHLMACFTCAKKLKKRNKPCPVCRQPIQMIVLTYFP

Orthologs for Hdm2 can be readily identified and are known in the art, for example, mouse (Genbank Accession No. AAB09030), rat (Genbank Accession No. NP_001101569.1), cat (Genbank Accession No. NP_001009346.1), dog (Genbank Accession No. AAG42840.0) and horse (Genbank Accession No. AAF28866.1).

In 2004, Vassilev and co-workers (Hoffman-La Roche Inc., Nutley, N.J.) described a class of antagonists that inhibited the murine double min 2 (MDM2)-p53 complex. These antagonists are a group of cis-imidazoline analogues designated as the Nutlins. Through x-ray crystallography, the MDM2-p53 complex showed a well defined hydrophobic cleft which represented the binding site for p53. In addition, the structure revealed that this cleft was filled by only three side chains of the helical region of p53: Phe19, Leu26 and Trp23. This observation led to the possibility that a small molecular inhibitor could mimic these three amino acids and their orientation. The inhibitor could disrupt the MDM2-p53 interaction by binding specifically in this cleft, liberating functional p53. A class of small molecules, called Nutlins, were found to bind specifically into the p53-binding pocket of Mdm2/Hdm2, thereby preventing Mdm2 interaction with p53 and inhibiting Mdm2-dependent degradation of p53. Nutlin-3a (RG7112/RO5045337) is currently in clinical trials for certain tumors in which the Hdm2/p53 pathway is intact (Secchiero P et al., 2011 Curr Pharm Des, 17:569-577). Furthermore, an ophthalmic formulation of Nutlin-3a has been developed (Brennan R C et al., 2011 Cancer Res, 71:4205-4213). The results presented below demonstrate that the correlation between the PDGFRα-mediated decline in the level of p53 and development of PVR is causally related, and that Nutlin-3a-mediated stabilization of p53 prevents PVR.

Nutlin-3a (RG7112/RO5045337) is a small molecule that is currently in clinical trials for certain types of cancer. Specifically, Nutlin-3 [(±)-4-[4,5-Bis(4-chlorophenyl)-2-(2-isopropoxy-4-methoxy-phenyl)-4,5-dihydro-imidazole-1-carbonyl]-piperazin-2-one] is a cis-imidazoline analog which inhibits the interaction between mdm2 and tumour suppressor p53. Nutlin-3 is arbitrarily referred to as enantiomer a because it appears as the first peak from chiral purification of racemic nutlin-3. It acts by preventing a decline in the level of p53, which is a transcription factor that is mutated in many, but not all tumors that occur in humans. By inhibiting the interaction between mdm2 and p53, Nutlin-3 stabilizes p53, and selectively induces a growth-inhibiting state called "senescence" in cancer cells. Specifically, in those tumors in which p53 remains intact (normal/wild type p53), Nutlin-3a prevents proliferation, and promotes the apoptosis/senescence of the tumor cells.

Nutlins are cis-imidazoline analogs which inhibit the interaction between mdm2 and tumour suppressor p53. Nutlin-3 ((±)-[4-[4,5-Bis(4-chlorophenyl)-2-(2-isopropoxy-4-methoxy-phenyl)-4,5-dihydro-imidazole-1-carbonyl]-piperazin-2-one]) has the following chemical structure:

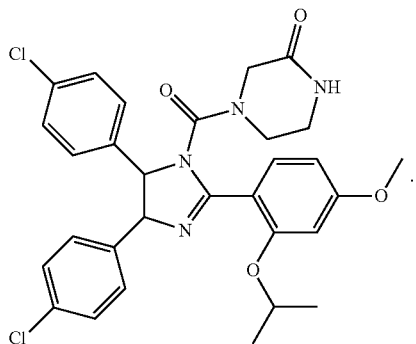 [SMILES: COc1ccc(C2=NC(c3ccc(Cl)cc3)C(c3ccc(Cl)cc3)N2C(=O)N2CCNC(=O)C2)c(OC(C)C)c1]

Cis-isomers of nutlin-3 are:

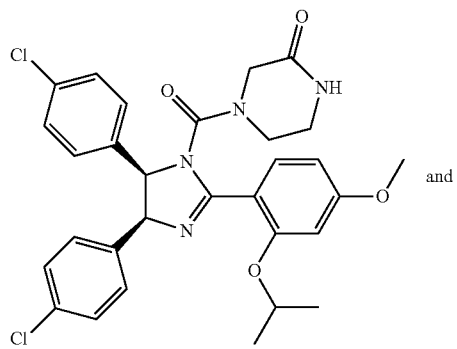

and

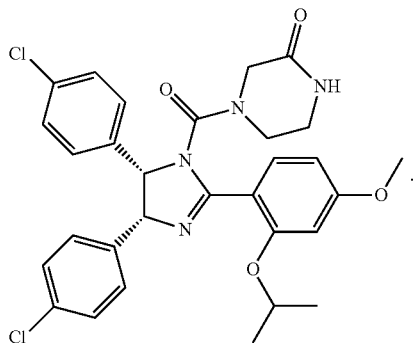

Trans-isomers of this compound are:

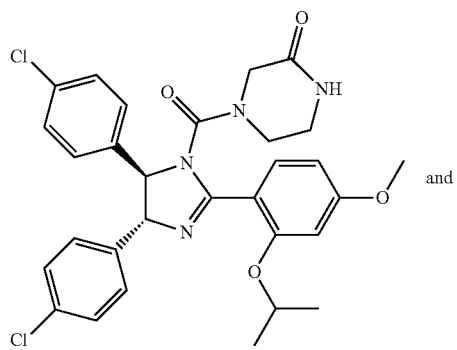

and

-continued

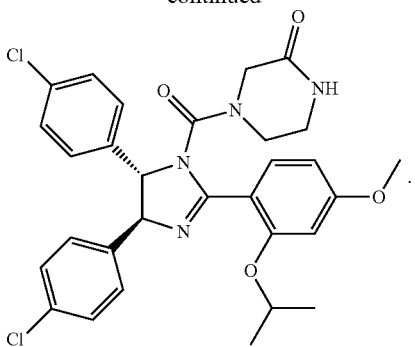

Nutlin-3a is arbitrarily referred to as enantiomer "a" because it appears as the first peak from chiral purification of racemic nutlin-3. Nutlin-3a acts by preventing a decline in the level of p53, which is a transcription factor that is mutated in many, but not all tumors that occur in humans. By inhibiting the interaction between mdm2 and p53, Nutlin-3a stabilizes p53, and selectively induces a growth-inhibiting state called "senescence" in cancer cells. Specifically, in those tumors in which p53 remains intact (normal/wild type p53), Nutlin-3a prevents proliferation, and promotes the apoptosis/senescence of the tumor cells.

Analogs of nutlin-3 may be a compound of formula (I):

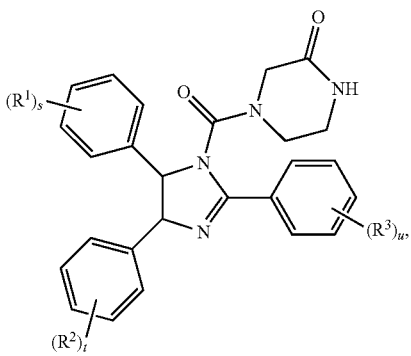

(I)

wherein
$R^1$ is independently selected from F, Cl, Br, and I;
$R^2$ is independently selected from F, Cl, Br, and I;
$R^3$ is independently selected from hydrogen, $C_1$-$C_6$ alkyl, and $C_1$-$C_6$-alkoxy;
s is 0, 1, 2, 3, 4, or 5;
t is 0, 1, 2, 3, 4, or 5; and
u is 0, 1, 2, 3, 4, or 5;
or a pharmaceutically acceptable salt, solvate, or prodrug thereof.

Analogs of nutlin-3 may be a compound of formula (II):

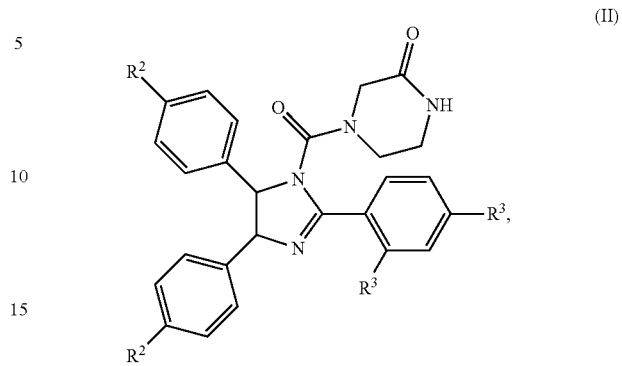

(II)

wherein
$R^1$ is independently selected from F, Cl, Br, and I;
$R^2$ is independently selected from F, Cl, Br, and I; and
$R^3$ is independently selected from hydrogen, $C_1$-$C_6$ alkyl, and $C_1$-$C_6$-alkoxy;
or a pharmaceutically acceptable salt, solvate, or prodrug thereof.

In one aspect, $R^1$ of formula (I) or (II) is Cl. In one aspect, $R^2$ of formula (I) or (II) is Cl. In another aspect, $R^3$ is methoxy or isopropyloxy.

As used herein, "alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

The term "alkoxy" includes substituted and unsubstituted alkyl groups covalently linked to an oxygen atom. Examples of alkoxy groups include methoxy, ethoxy, isopropyloxy, propoxy, butoxy, and pentoxy groups.

"Isomer" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center". "Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center.

Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Pharmaceutically acceptable salt" of a compound means a salt that is pharmaceutically acceptable and that possesses the desired pharmacological activity of the parent compound.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. The analogs described herein also retain similar function to Nutlin-3a, in which the analog also reduces or inhibits the interaction or association between p53 and Hdm2, or increases intraocular p53 levels.

As used herein, "blocking the interaction or association" or "inhibiting or reducing binding" refers to preventing or reducing the direct or indirect association of one or more molecules, peptides, or proteins; or preventing or reducing the normal activity of one or more molecules, peptides, or proteins. The interaction, association, or binding is covalent, non-covalent, or ionic.

The present invention also provides functional derivatives of analogs of Nutlin-3a. As used herein, "functional analogs" of Nutlin-3a refers to small molecules, antibodies, polypeptides, or polynucleotides that inhibit or reduce the interaction or association between p53 and Hdm2. Preferably, the functional analog binds in the p53-binding pocket of Hdm2 and inhibits or reduces interaction, association or binding between p53 and Hdm2. Functional analogs of Nutlin-3a can be identified by screening methods known in the art. Suitable screening assays may utilize techniques known in the art such as two hybrid assay, fluorescence resonance energy transfer (FRET), bioluminescence resonance energy transfer (BRET), protein-fragment complementation (PCA), or co-immunoprecipitation assay which detect protein-protein interactions, to detect interaction of p53 and Hdm2, or inhibition or reduction of p53-Hdm2 binding.

In particular, a screening assay to identify functional analogs was described in Vassilev et al. (2004, Science, 303:845-848), hereby incorporated by reference in its entirety. For example, the screening assay comprises assaying (i) stabilization and accumulation of p53 protein, (ii) activation of Hdm2 expression, or (iii) activation of other p53-regulated genes and the p53 pathway. For example, the skilled artisan, using the amino acid sequences disclosed herein for p53 and Hdm2 could use recombinant DNA methods well known in the art to construct expression vectors and in vitro translate the p53 and Hdm2 proteins. Incubation of the proteins with putative analogs of Nutlin or a library of agents to be screened can be performed with optimal conditions determined by the skilled artisan. Co-immunoprecipitation, immunoaffinity purification, western blotting or other methods well known in the art are then used to assess the binding between p53 and Hdm2, or the inhibition or reduction of binding by the introduction of the putative Nutlin analog. In other embodiments, stabilization and accumulation of p53 protein levels can be determined in vitro, through immunoblotting techniques utilizing p53-specific antibodies. In another embodiment, the activation of other p53-regulated genes and the p53 pathway, such as MDM2, apoptosis genes PUMA and NOXA, cell cycle regulators p21, and p53 itself can be assessed by determining or quantifying the expression levels by mRNA or protein.

Pharmaceutical Compositions

For administration to a subject such as a human or other mammal (e.g., companion, zoological or livestock animal), the Nutlin or analog thereof is desirably formulated into a pharmaceutical composition containing the active agent in admixture with one or more pharmaceutically acceptable diluents, excipients or carriers. Examples of such suitable excipients for can be found in U.S. Publication 2009/0298785 (incorporated by reference herein in its entirety), the *Handbook of Pharmaceutical Excipients*, 2nd Edition (1994), Wade and Weller, eds. Acceptable carriers or diluents for therapeutic use are well-known in the pharmaceutical art, and are described, for example, in Remington: the Science and Practice of Pharmacy, 20th Edition (2000) Alfonso R. Gennaro, ed., Lippincott Williams & Wilkins: Philadelphia, Pa. Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical composition can contain as, or in addition to, the carrier, excipient or diluent any suitable binder(s), lubricant(s), suspending agent(s), coating agent(s), solubilizing agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents can be provided in the pharmaceutical composition, Examples of preservatives include sodium benzoate, sorbic acid and esters of p-hydroxybenzoic acid. Antioxidants and suspending agents can be also used.

A person of ordinary skill in the art can easily determine an appropriate dosage to administer to a subject without undue experimentation. Typically, a physician will determine the actual dosage that will be most suitable for an individual subject based upon a variety of factors including the activity of the specific compound employed, the metabolic stability and length of action of the compound, the age, body weight, general health, diet, mode and time of administration, rate of excretion, drug combination, the severity of the particular condition, and the individual undergoing therapy. To determine a suitable dose, the physician or veterinarian could start doses levels lower than that required in order to achieve the desired therapeutic effect and gradually increase the dosage until the desired effect is achieved. This is considered to be within the skill of the artisan and one can review the existing literature on a specific agent to determine optimal dosing.

The compositions described herein comprising a Nutlin or an analog thereof can be administered to a subject via intravitreally of subconjunctivally. In some embodiments, the composition is administered in the form of a liquid (e.g., drop or spray) or gel suspension. Alternatively, the composition is applied to the eye via liposomes or infused into the tear film via a pump-catheter system. Further embodiments embrace a continuous or selective-release device, for example, membranes such as, but not limited to, those employed in the OCUSERT System (Alza Corp., Palo Alto, Calif.) In an alternative embodiment, the p53 activator is contained within, carried by, or attached to a contact lens, which is placed on the eye. Still other embodiments embrace the use of the composition within a swab or sponge, which is applied to the ocular surface.

In some cases, the composition further comprises a pharmaceutically acceptable carrier, e.g., a pharmaceutically acceptable salt. Suitable ocular formulation excipients include FDA approved ophthalmic excipients, e.g., emulsions, solutions, solution drops, suspensions, and suspension drops, a list of which is provided in Table 1. Other suitable classifications include gels, ointments, and inserts/implants. Table 1 provides maximum percentages, when available, for the various formulation types.

Exemplary excipients for use in optimizing ocular formulations include alcohol, castor oil, glycerin, polyoxyl 35 castor oil, Tyloxapol, polyethylene glycol 8000 (PEG-8000), ethanol, glycerin, cremaphor, propylene glycol (pG), polypropylene glycol (ppG), and polysorbate 80. In some cases, citrate buffer and sodium hydroxide are included to adjust pH. Preferably, the formulation for ocular delivery of nutlin-3a comprises 5% cremaphor, 10% pG, 15% pPG, and 70% phosphate buffered saline (PBS).

TABLE 1

| Excipient/Co-solvent | Exemplary Percentage According to the FDA Excipient Database http://www.accessdata.fda.gov/scripts/cder/iig/index.cfm |
|---|---|
| Acetic Acid | 0.2 (solution), 0.9% (drops) |
| Alcohol | 0.5% (solution), 1.4% (solution, drops) |
| Alcohol, dehydrated | 0.5% (solution), 0.5% (solution, drops) |
| Ammonium hydroxide | N/A (solution; solution, drops) |
| Anyhydrous trisodium citrate | N/A (solution) |
| Antipyrine | 0.1% (solution) |
| Benzalkonium chloride | 2% (solution), 0.9% (drops) |
| Benzododecinium | 0.012% (solution) |
| Boric acid | 0.1% (emulsion), 37.2% (solution), 1.9% (solution, drops), 1% (suspension), 0.6% (suspension drops) |
| Caffeine | 2% (solution) |
| Calcium chloride | 0.02% (solution, drops) |
| Carbomer 1342 | 0.05% (emulsion) |
| Creatinine | 0.5% (solution), 0.2% (solution, drops) |
| Carbomer 934P | 0.45% (suspension, drops) |
| Carbomer Homopolymer Type B | 0.5% (suspension), 0.45% (suspension, drops) |
| Carboxymethylcellulose sodium | 0.5% (solution, drops) |
| Castor oil | 5% (emulsion) |
| Cetyl alcohol | 0.5% (suspension) |
| Chlorobutanol | 0.5% (solution), 0.2% (solution, drops) |
| Cholesterol | N/A (powder, for suspension) |
| Citric acid | 0.2% (solution), 0.05% (solution, drops) |
| Citric acid monohydrate | 0.05% (solution; solution, drops) |
| Diethanolamine | N/A (solution) |
| Divinylbenzene styrene copolymer | 0.75% (suspension, drops) |
| Edetate disodium | 10% (solution), 0.1% (solution, drops), 0.13% (suspension), 0.101% (suspension, drops) |
| Edetate sodium | 0.02% (emulsion), 0.1% (solution), 0.02% (suspension) |
| Gellan gum | 0.6% (solution) |
| Glycerin | 2.2% (emulsion), 3% (solution), 2.6% (solution, drops), 2.5% (suspension; suspension, drops) |
| Glyceryl stearate | 0.5% (suspension) |
| Hydrocarbon gel, plasticized | N/A (suspension) |
| Hydrochloric acid | 1.06% (solution), 0.17% (solution, drops) |
| Hydroxyethyl cellulose | 0.5% (solution; solution, drops), 0.25% (suspension), 0.35% (suspension, drops) |
| Hydroxyethyl methylcellulose | 0.5% (solution) |
| Hypromellose 2910 | 0.5% (solution; suspension; suspension, drops) |
| Hypromelloses | 50% (solution), 0.5% (solution, drops; suspension), 0.6% (suspension, drops) |
| Lauralkonium chloride | 0.005% (solution, drops) |
| Lauroyl sarcosine | 0.03% (suspension, drops) |
| Light mineral oil | N/A (suspension) |
| Magnesium chloride | 0.03% (powder, for solution), 0.0065% (solution, drops) |
| Mannitol | 23% (solution), 4.6% (solution, drops), 2.4% (suspension), 4% (suspension, drops) |
| Methylcellulose | 0.5% (solution) |
| Methylparaben | 0.05% (solution; solution, drops; suspension; suspension, drops) |
| Mineral oil | 0.1% (suspension) |
| Nitric acid | N/A (solution) |

TABLE 1-continued

| Excipient/Co-solvent | Exemplary Percentage According to the FDA Excipient Database http://www.accessdata.fda.gov/scripts/cder/iig/index.cfm |
|---|---|
| Nitrogen | N/A (solution) |
| Nonoxynol-9 | 0.125% (solution) |
| Nonoxynol-40 | 0.05% (solution), 0.01 (solution, drops) |
| Octylphenol polymethylene | N/A (solution) |
| Phosphoric acid | N/A (solution, drops) |
| Polidronium chloride | 0.0005% (solution, drops) |
| Poloxamer 188 | 0.1% (solution; solution, drops) |
| Poloxamer 407 | 0.2% (solution), 0.16% (solution, drops), 0.101% (suspension, drops) |
| Polycarbophil | 0.9% (solution), 0.859% (suspension, drops) |
| Polyethylene glycol 300 | N/A (solution) |
| Polyethylene glycol 8000 | 2% (solution) |
| Polyoxyl 35 castor oil | 5% (solution; solution, drops) |
| Polyoxyl 40 hydrogenated castor oil | 0.5% (solution, drops) |
| Polyoxyl 40 stearate | 7% (solution), 0.5% (suspension) |
| Polypropylene glycol | 15% (solution) |
| Polysorbate 20 | 0.05% (suspension) |
| Polysorbate 80 | 4% (emulsion), 0.2% (solution), 1% (solution, drops), 0.1% (suspension; suspension, drops) |
| Polyvinyl alcohol | 1.4% (solution; solution, drops; suspension; suspension, drops) |
| Potassium acetate | 4% (powder, for solution) |
| Potassium chloride | 22.2% (solution), 0.14% (solution, drops), |
| Potassium phosphate, monobasic | 0.2% (solution), 0.065% (solution, drops), 0.44% (suspension) |
| Potassium sorbate | 0.47% (solution) |
| Povidone K29/32 | 1.8% (solution) |
| Povidone K30 | 2% (solution), 0.6% (suspension) |
| Povidone 90 | 1.2% (solution) |
| Propylene glycol | 10% (solution), 0.75% (solution, drops), 5% (suspension), 1% (suspension, drops) |
| Propylparaben | 0.015% (solution; solution, drops), 0.01% (suspension; suspension, drops) |
| Sodium acetate | 0.05% (emulsion), 0.35% (solution), 1.279% (solution, drops) |
| Sodium bisulfite | 0.1% (solution; solution, drops); 0.06% (suspension) |
| Sodium borate | 0.543% (solution), 1.1% (solution, drops), 0.0285% (suspension, drops) |
| Sodium borate decahydrate | 0.15% (solution), 0.095% (solution, drops) |
| Sodium carbonate | 1% (solution) |
| Sodium chloride | 55% (solution), 0.9% (solution, drops), 0.85% (suspension), 0.68% (suspension, drops) |
| Sodium citrate | 2% (solution), 2.2% (solution, drops), 0.3% (suspension), 0.45% (suspension, drops) |
| Sodium hydroxide | 0.397% (emulsion), 0.1% (solution) |
| Sodium metabisulfite | 0.2% (solution), 0.25% (solution, drops), 0.1% (suspension, drops) |
| Sodium nitrate | 1.18% (solution) |
| Sodium phosphate | 0.81% (solution), 0.29% (solution, drops), 0.2% (suspension) |
| Sodium phosphate dihydrate | 0.03% (solution) |
| Sodium phosphate, dibasic | 0.29% (solution), 0.43% (suspension) |
| Sodium phosphate, dibasic, anhydrous | 1.28% (solution), 1.4% (solution, drops), 0.25% (suspension) |
| Sodium phosphate, dibasic, dihydrate | 1.081% (solution), 1.201% (solution, drops) |
| Sodium phosphate, dibasic, heptahydrate | 2.15% (solution), 2.5% (solution, drops), 0.866% (suspension), 0.431% (suspension, drops) |
| Sodium phosphate, monobasic | 0.19% (solution), 0.01% (solution, drops) |
| Sodium phosphate, monobasic, anhydrous | 0.725% (solution), 0.78% (solution, drops), 0.65% (suspension), 0.056% (suspension, drops) |
| Sodium phosphate, monobasic, dihydrate | 1.158% (solution), 1.053% (solution, drops) |
| Sodium phosphate, monobasic, monohydrate | 0.54% (solution), 0.721% (solution, drops), 0.538% (suspension) |
| Sodium sulfate | 0.226% (solution), 1.2% (suspension) |
| Sodium sulfate anhydrous | 0.152% (solution), 0.17% (solution, drops), 1.2% (suspension) |
| Sodium sulfate decahydrate | 0.09% (solution, drops) |
| Sodium sulfite | 0.2% (solution, drops) |
| Sodium thiosulfate | 5% (solution), 0.31% (solution, drops), 0.32% (suspension), 0.314% (suspension, drops) |
| Sorbic acid | 0.1% (emulsion), 0.2% (solution; solution, drops) |
| Sorbitol | 0.2% (solution), 0.25% (solution, drops) |
| Stabilized oxychloro complex | 0.005% (solution, drops) |
| Sulfuric acid | 0.02% (solution, drops) |
| Thimerosal | 0.01% (solution; solution, drops), 0.004% (suspension), 1% (suspension, drops) |
| Tocophersolan | 0.5% (solution, drops) |
| Trisodium citrate dihydrate | 0.3% (solution), 0.294% (solution, drops) |

TABLE 1-continued

| Excipient/Co-solvent | Exemplary Percentage According to the FDA Excipient Database http://www.accessdata.fda.gov/scripts/cder/iig/index.cfm |
|---|---|
| Triton 720 | N/A (solution) |
| Tromethamine | 0.936% (solution), 0.75% (solution, drops) |
| Tyloxapol | 0.1% (solution; solution, drops), 0.3% (suspension; suspension, drops) |
| Xanthan gum | 0.6% (solution) |
| Zinc chloride | 0.0025% (solution, drops) |

Preferably, the compositions are delivered by intravitreal injection or subconjunctival administration.

As described in detail below, suppressing expression of p53 was a required event in two assays of PVR, namely, PDGFRα-mediated contraction of cells in a collagen gel and retinal detachment in an animal model of PVR. Furthermore, as described in detail below, preventing the decline in the level of p53 with agents such as Nutlin-3a protected from retinal detachment, which is the most vision-compromising component of PVR. Finally, as described herein, Nutlin-3a is effective in the clinical setting, as the small molecule prevented human PVR vitreous-induced contraction of cells isolated from a patient PVR membrane.

Figure 2A:
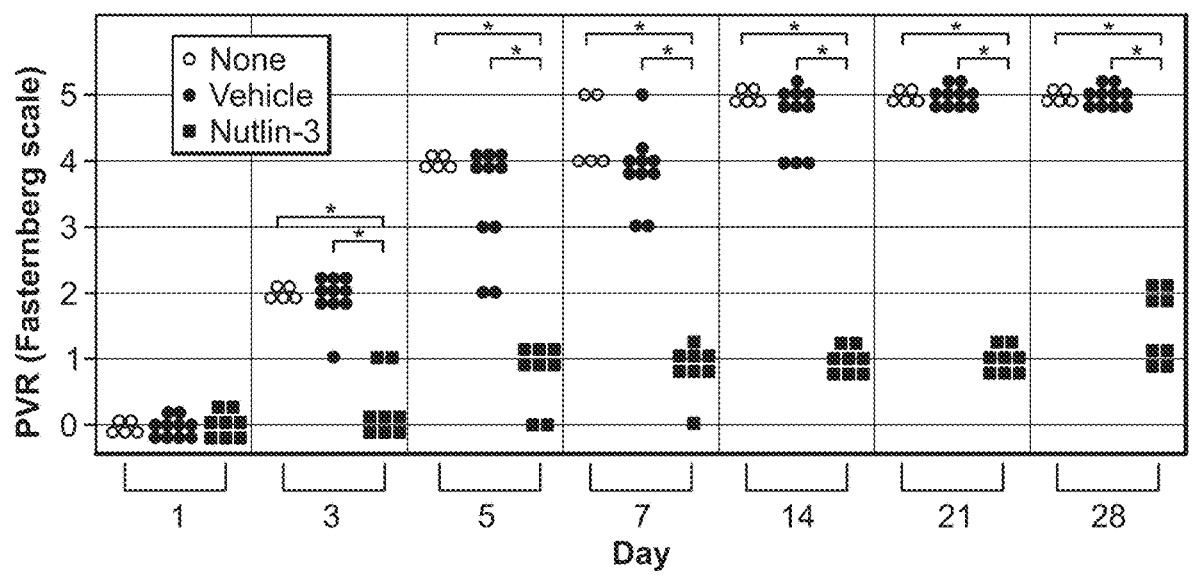
FIGS. 2A-2B include a dot plot and a series of photomicrographs showing that Nutlin -3a prevented retinal detachment and elevated p53 in epiretinal membranes.

As described below, Nutlin-3a was administered in a series of intravitreal injections. While this approach completely prevented retinal detachment, 50% of the rabbits developed vitreal traction (stage 2) (FIG. 2A). Since the last injection of Nutlin-3a was 23 days prior to the end of the experiment, the level of Nutlin-3a may have dropped below the therapeutic range. The recently-developed ocular formulation of Nutlin-3a, which can be administered as a subconjunctival injection (Brennan R C et al., 2011 Cancer Res, 71:4205-4213), is also suitable to achieve Nutlin-3a-mediated PVR prophylaxis.

As described in detail below, Nutlin-3a treatment very effectively prevented retinal detachment, and also slowed formation of membranes (stage 1) (FIG. 2A), both of which are of clinical benefit. It was surprising that membranes were able to form in Nutlin-3a animals, because Nutlin-3 activates the p53 pathway (Vassilev L T et al., 2004 Science, 303:844-848), which counters cellular events that are intrinsic to membrane formation such as proliferation and survival (Lei H et al., 2010 Exp Eye Res, 90:376-381). However, this observation is consistent with reports that elevating p53 does not always cause apoptosis and/or cell cycle arrest (Giono L E et al., 2007 Mol Cell Biol, 27:4166-4178; Mendrysa S M et al., 2003 Mol Cell Biol, 23:462-472; Mendrysa S M et al., 2006 Genes Dev, 20:16-21). For instance, p53 is transiently elevated in mitotic cells of normal tissue in healthy animals, and fails to engage the p53 pathway because p53 is held in check by post-translational modifications (Loewer A et al., 2010 Cell, 142:89-100).

Figure 6:
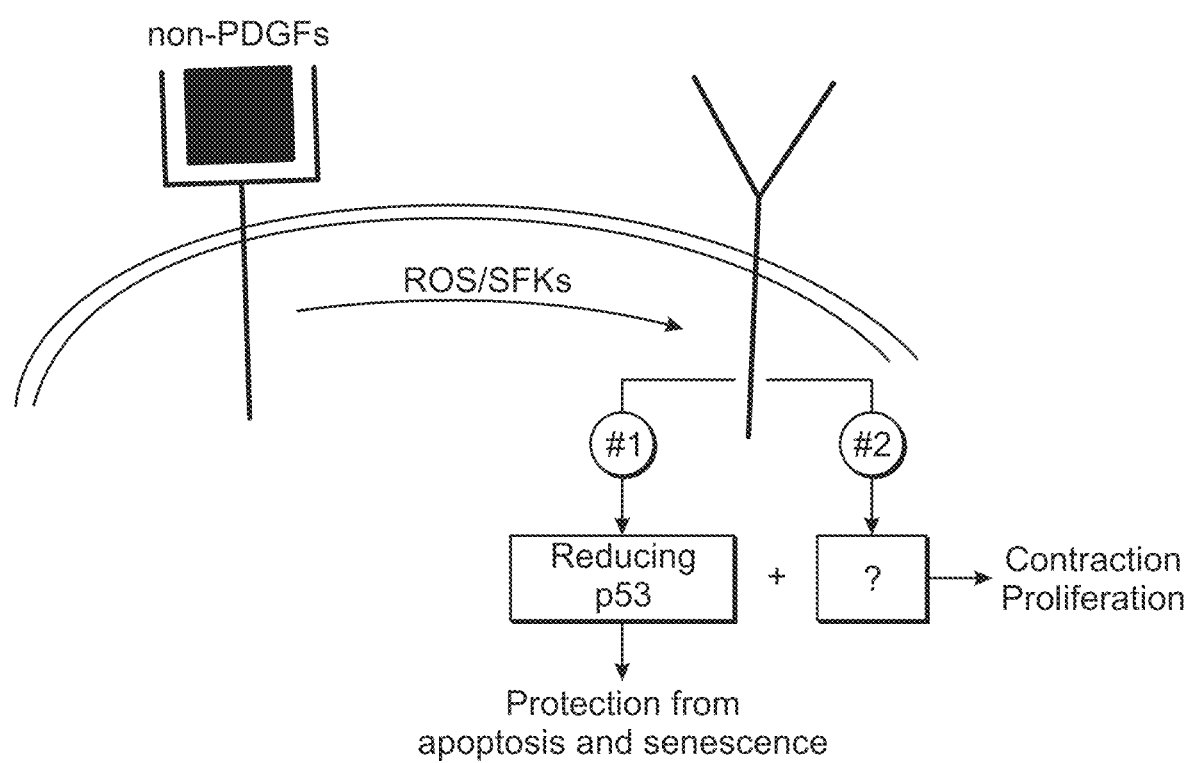
FIG. 6 is a schematic representation showing that RV engaged PDGFRα, which triggered two signaling pathways that drive cellular response intrinsic to PVR. Signaling pathway #1 leads to a reduction in the level of p53, and this is sufficient for protection from apoptosis and senescence. Contraction and proliferation require an additional set of signaling events that constitute pathway #2.

The results described herein reveal that cellular responses associated with PVR do not have the same requirements. Contraction and proliferation require a decline in the level of p53 and a second PDGFRα-mediate event(s), whereas protection from apoptosis and senescence proceed when only p53 is suppressed (FIG. 6). Furthermore, while all 4 responses were completely dependent on expression of PDGFRα, contraction required the lowest level. This low threshold for PDGFRα expression and ability of contraction to proceed when other cellular response are impaired provide a plausible explanation for why therapies targeting other cellular responses have not been successful (Wiedemann P et al., 1998 Am J Ophthalmol, 126:550-559; Asaria R H et al., 2001 Ophthalmology, 108:1179-1183; Schiff W M et al., 2007 Arch Ophthalmol, 125:1161-1167).

As described in detail below, epiretinal membranes formed in rabbits injected with cells that were unable to suppress p53 efficiently (sh PDGFRα), which was required for RV-mediated proliferation and viability, cellular events that are thought to be essential for membrane formation. Previous reports have shown that proliferation-incompetent cells induce PVR provided that they are injected at a sufficiently high level (Fastenberg D M et al., 1982 Am J Ophthalmol, 93:565-572). Thus, membranes may have formed in rabbits injected with sh PDGFRα cells because enough of them were injected.

The examples below demonstrate that both molecular and pharmacological approaches indicate that reducing the level of p53 was permissive for retinal detachment, a process that involves contraction of the retina-associated membrane. A simple explanation for this phenomenon is that p53 suppresses the expression of genes that are required for retinal detachment. For instance, p53 may inhibit production of those extracellular matrix proteins that are required for contraction of the membrane (Iotsova V et al., 1996 Cell Growth Differ, 7:629-634). However, such an explanation appears inadequate for the in vitro contraction assays, which contained ample extracellular matrix proteins that are conducive for contraction. p53 may down regulate expression of integrins such as β1 (Qiu J et al., 2011 Mol Cell Biochem, 357:125-133), whose interaction with extracellular matrix proteins is essential for contraction. Alternatively, there may be a connection to EMP2 (epithelial cell membrane protein) and FAK (focal adhesion kinase), which are essential for contraction of collagen gels and strongly implicated in PVR (Morales S A et al., 2009 Invest Ophthalmol Vis Sci, 50:4949-4956; Morales S A et al., 2007 Exp Eye Res, 85:790-798; Morales S A et al., 2009 Invest Ophthalmol Vis Sci, 50:462-469; Morales S A et al., 2011 Invest Ophthalmol Vis Sci, 52:5465-5472; Telander D G et al., 2011 Curr Eye Res, 36:546-552).

Finally, just as p53 suppresses cell cycle progression (Levine A J et al., 1991 Nature, 351:453-456), the results presented herein indicate that p53 is a checkpoint of retinal detachment. In contrast to genetic lesion of the p53 pathway that are present in approximately 50% of solid tumors (Hainaut P and Hollstein M, 2000 Adv Cancer Res, 77:81-137, epigenetic, environmental factors that result in non-canonical activation of PDGFRα drive p53-dependent blinding diseases such as PVR.

EXAMPLES

Example 1: Materials and Methods

The materials and methods used in the examples described herein are set forth below.

Major Reagents and Cell Culture

The phospho-Y742 PDGFRα antibody was raised against the phospho-peptide [KQADTTQpYVPMLDMK (SEQ ID NO: 3), where the lower case "p" represents the phosphorylated Tyrosine residue] (Lei H et al., 2010 Am J Pathol, 177:132-140). The Ras GTPactivating protein (RasGAP) antibody was crude rabbit antiserum against a GST fusion protein including the SH2-SH3-SH2 region of the human RasGAP (Rosenkranz S et al., 1999 J Biol Chem, 274: 28335-28343). Antibodies against PDGFRα, phospho-Akt (S473), Akt, and p53 were purchased from Cell Signaling Technology (Beverly, Mass.). Secondary antibodies (horseradish peroxidase-conjugated goat anti-rabbit immunoglobulin G, and goat anti-mouse immunoglobulin G) were purchased from Santa Cruz Biotechnology (Santa Cruz, Calif.). Enhanced chemiluminescent substrate for detection of horseradish peroxidase was from Pierce Protein Research Products (Rockford, Ill.). ApoAlert annexin VFITC apoptosis kit and in situ β-galactosidase assay kit were purchased from Clontech Laboratories, Inc. (Mountain View, Calif.) and Agilent Technologies, (Santa Clara, Calif.), respectively. Nutlin-3a was purchased from Cayman Chemical (Ann Arbor, Mich.). Normal rabbit vitreous (RV) was prepared from frozen rabbit eyeballs as previously described (Lei H et al., 2009 J Biol Chem, 284:6329-6336). The level of PDGFs in RV is either very low, or below the level of detection (Lei H et al., 2007 Invest Ophthalmol Vis Sci, 48:2335-2342; Pennock S et al., 2011 Am J Pathol, 179: 2931-2940).

RPEM cells are RPE cells derived from a human epiretinal membrane, as previously described (Wong C A et al., 2002 Can J Ophthalmol, 37:211-220). Primary rabbit conjunctival fibroblasts (RCFs) were obtained and cultured as described previously (Ikuno Y et al., 2002 Invest Ophthalmol Vis Sci, 43:2406-2411). RCFs that stably expressed the shRNA targeting vector specific for GFP, PDGFRα, p53 or PDGFRα and p53 were designated sh GFP, sh PDGFRα sh p53 and sh PDGFRα/p53, respectively. F cells are immortalized mouse embryo fibroblasts derived from PDGFR knock-out mice that do not express either of the two PDGFR genes, Fα and Fβ cells are F cells in which PDGFRα or PDGFRβ has been re-expressed (Andrews A et al., 1999 Invest Ophthalmol Vis Sci, 40:2683-2689).

Knockdown of PDGFRα and p53

Oligos (GCCAGCTCTTATTACCCTCTA (SEQ ID NO: 4)) for PDGFRα, (CGGGCGTAAACGCTTCGAGAT (SEQ ID NO: 5)) for p53 and (ACAACAGC-CACAACGTCTATA (SEQ ID NO: 6)) for GFP in a hairpin-pLKO.1 retroviral vector respectively, the packaging plasmid (pCMVdR8.91), the envelope plasmid (VSV-G/pMD2.G) and 293T packaging cells used. The shRNA lentiviruses were prepared as described previously (Lei H et al., 2011 Mol Cell Biol, 31:1788-1799). The viruses were used to infect RCF cells. Successfully infected cells were selected on the basis of their ability to proliferate in media containing puromycin (1 µg/ml). The resulting cells were characterized by western blot analysis using antibodies against PDGFRα, p53 and RasGAP (loading control).

Western Blot

Cells were grown to 90% confluence in serum-containing medium, and then incubated for 24 hr in medium without serum. Cells were stimulated (as detailed for each experiment), washed twice with ice-cold phosphate buffered saline (PBS), and lysed in extraction buffer (10 mM Tris-HCl, pH 7.4, 5 mM EDTA, 50 mM NaCl, 50 mM NaF, 1% Triton X-100, 20 µg/ml aprotinin, 2 mM Na3VO4, 1 mM phenylmethylsulfonyl fluoride). Lysates were clarified by centrifugation at 13,000×g, 4° C. for 15 min. Equal amounts of protein were separated by 10% sodium dodecyl sulfate polyacrylamide gel electrophoresis (SDS-PAGE), transferred to PVDF membranes, and then subjected to western blot analysis using indicated antibodies. Signal intensity was determined by densitometry and analyzed with the Quantity One (Bio-Rad) software.

Collagen I Contraction Assay

Cells were trypsinized, washed and resuspended in 1.5 mg/ml of neutralized collagen I (INAMED, Fremont, Calif.) (pH 7.2) at a density of $1 \times 10^6$ cells/ml for RPEM or $5 \times 10^4$ cells/ml for RCFs. The mixture was aliquoted into wells of a 24-well plate that had been preincubated overnight with 5 mg/ml bovine serum albumin in PBS. The collagen solution was solidified by incubating at 37° C. for 90 min, and overlaid with medium containing the desired agents. The media were replaced every day, and the gel diameter was measured on day 3. The gel area was calculated using the formula $\pi r2$, where r is the radius of the gel.

Proliferation and Apoptosis Assays

Proliferation and apoptosis was assayed as previously described (Lei H et al., 2009 J Biol Chem, 284:6329-6336). Briefly, RCFs were seeded into 24-well plates at a density of 50,000 cells/well in DMEM+10% FBS. After 6 hrs the cells had attached; the medium was aspirated, the cells were rinsed twice with PBS and the cells were cultured in serum-free DMEM with or without RV (1:3 dilution). The media were replaced every day. On Day 3, the cells were counted in a hemocytometer. At least three independent experiments were performed. To monitor apoptosis, RCFs were seeded into 6 cm-dishes at a density of $1 \times 10^5$ cells per dish in DMEM+10% FBS. After the cells had attached the dishes, they were treated as described above in the proliferation Assay. On Day 3, the cells were harvested and stained with FITC-conjugated Annexin V and propidium iodide according to the instructions provided with the apoptosis kit (BD Biosciences, Palo Alto, Calif.). The cells were analyzed by flow cytometry in Coulter Beckman XL. At least three independent experiments were performed.

Senescence Assay

RCF cells were plated into a 12-well plate (10,000 cells/well) in DMEM (high glucose) supplemented with 10% FBS. After 6 hrs the medium was changed into DMEM with or without RV (1:3 dilution), and replenished every 24 hrs. On day 3, the β-galactosidase activity was assessed according to the manufacturer's instructions provide with the in situ β-galactosidase assay kit.

Rabbit Model for PVR

PVR was induced in Dutch Belted rabbits, purchased from Covance (Denver, Pa.), as previously described (Lei H et al., 2009 Invest Ophthalmol Vis Sci, 50:3394-3403). Briefly, a gas vitrectomy was performed by injecting 0.1 ml of perfluoropropane (C3F8) (Alcon, Fort Worth, Tex.) into vitreous. One week later, the right eye of rabbits was injected in one of two ways. For the experiment injecting RCFs expressing shRNAs, 0.1 ml of DMEM containing $1 \times 10^5$ RCFs that were modified as outlined in the legend were injected along with 0.1 ml rabbit platelet-rich plasma. For the Nutlin-3a experiment, all rabbits were injected with 0.1 ml of DMEM containing $1 \times 10^5$ unmodified RCFs, 0.1 ml rabbit platelet rich plasma and either not injected a third time, or injected with vehicle, or 0.1 ml of 200 µM Nutlin-3a. The vehicle or Nutlin-3a injection was repeated on day 3 and 5. The retinal status was evaluated with an indirect ophthalmoscope fitted with a +30 D fundus lens on day 1, 3, 5, 7, 14, 21 and 28. PVR was graded according to the Fastenberg scale of classification 41: stage 0, no disease;

stage 1, epiretinal membrane; stage 2, vitreoretinal traction without retinal detachment; stage 3, localized retinal detachment (1-2 quadrants); stage 4, extensive retinal detachment (2-4 quadrants without complete detachment); stage 5, complete retinal detachment. On day 28, animals were sacrificed, and eyes were enucleated and frozen at −80° C.

Immunohistochemistry

Rabbit eyeballs were fixed in 10% formalin for 48 hr and embedded in paraffin after dehydration. Subsequently, 4 μm paraffin sections were prepared, dewaxed in xylene and rehydrated in ethanol, diluted ethanol and deionized water. Antigen retrieval that was performed by boiling the slides for 20 min in a citrate-based buffer (Vector Laboratories Inc., Burlingame, Calif.). The endogenous peroxidase activity was blocked by incubation with 1% $H_2O_2$ in methanol for 10 min and the endogenous avidin and biotin binding sites were blocked by incubation with avidin and biotin blocking buffers (Vector Laboratories). The resulting sections were first incubated in blocking buffer containing 3% goat serum, and then in primary antibody (diluted 1:200 in blocking buffer, anti-p53 from ABcam [Cambridge, Mass.]) overnight at 4° C. Incubation with secondary antibody (biotinylated goat anti-mouse; ABcam) was for one hour at room temperature. Finally, the ABC reagent (Vector Laboratories) was added for 45 min and the sections were stained with DAB (Thermo Scientific, Rockford, Ill.). The sections were observed and photographed under a microscope.

Statistics

The experimental data were analyzed using an unpaired t test and one way ANOVA and/or post tests. A p value of less than 0.05 was considered statistically significant.

Example 2: Suppressing p53 was Essential for RV-Induced Contraction, and Retinal Detachment RV contains a variety of non-PDGFs that indirectly activate PDGFRα and thereby chronically stimulate Akt (Lei H et al., 2011 Mol Cell Biol, 31:1788-1799), which phosphorylates and activates Mdm2 (Zhou B P et al., 2001 Nat Cell Biol, 3:973-982) that mediates a decline in the level of p53 (Ogawara Y et al., 2002 J Biol Chem, 277:21843-21850; Gottlieb T M, et al., 2002 Oncogene, 21:1299-1303; Haupt Y et al., 1997 Nature, 387:296-299). Nutlin-3a antagonizes the interaction of Mdm2 and p53, and thereby prevents Mdm2-mediated reduction of p53 (Vassilev L T et al., 2004 Science, 303:844-848). Because of these properties, it was determined whether Nutlin-3a would prevent RV-mediated reduction in the level of p53, contraction of cells in collagen gels and protect rabbits from developing PVR. Primary rabbit conjunctival cells (RCFs) were utilized in these experiments because they robustly contract collagen gels and induce PVR.

Figure 1B:
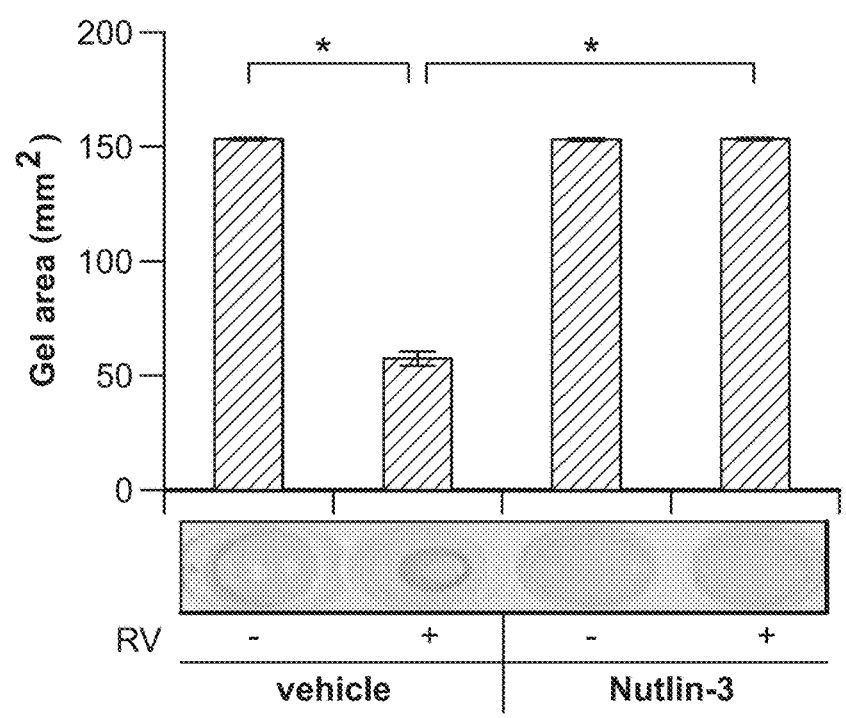
Figure 8A:
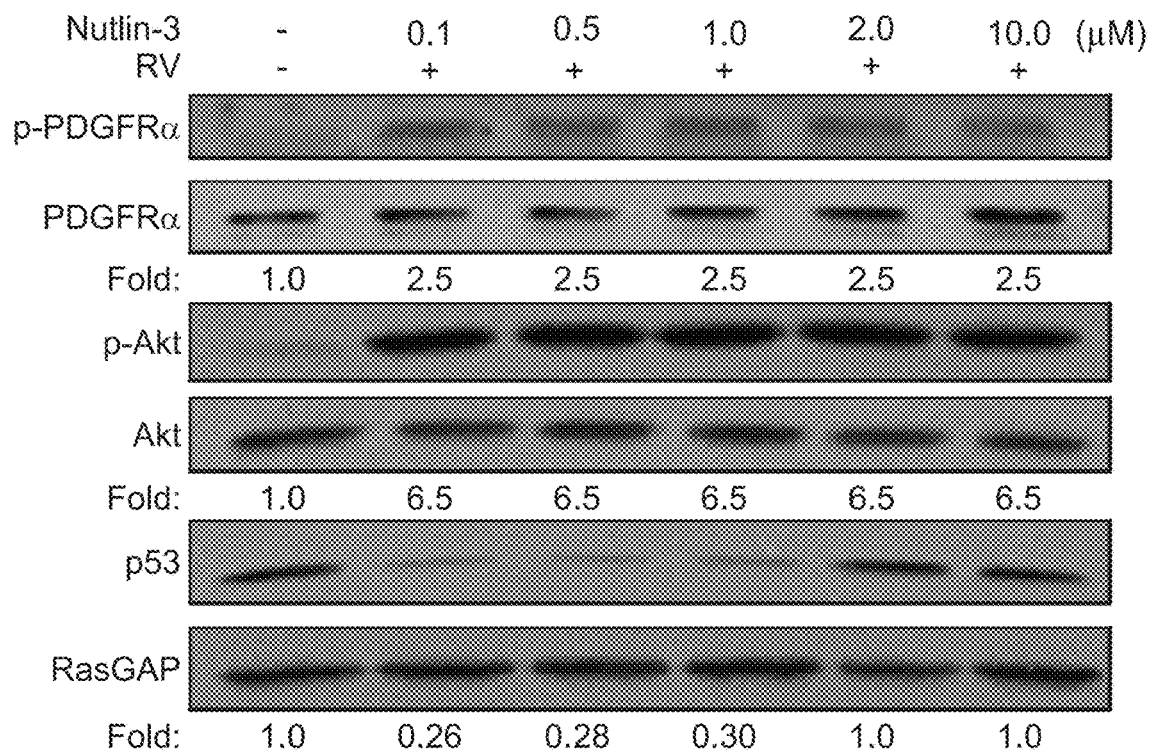
Figure 8B:
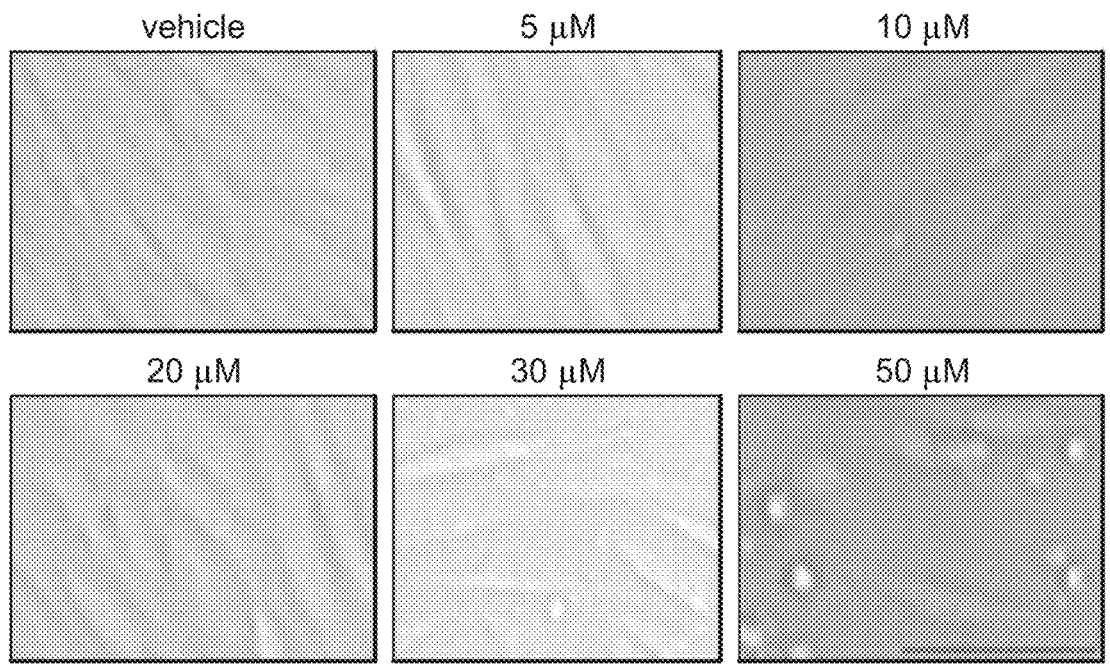

Nutlin-3a effectively blocked the RV-mediated decline in the level of p53 and contraction of collagen gels (FIGS. 1A-1B). As expected, it had no effect on RV-induced phosphorylation of PDGFRα or activation of Akt (FIG. 1A), events that are upstream of the known action of Nutlin-3a. The minimum dose to prevent the RV-induced reduction of p53 was 2 micromolar (FIG. 8A), whereas the maximum tolerated dose was 30 micromolar (FIG. 8B). Moreover, multiple intravitreal injection of Nutlin-3a of up to 20 micromolar did not produce overt signs of retinal toxicity (FIGS. 9A-9B, and data not shown). These results set the stage to test if Nutlin-3a could prevent retinal detachment in an animal model of PVR.

Figure 2B:
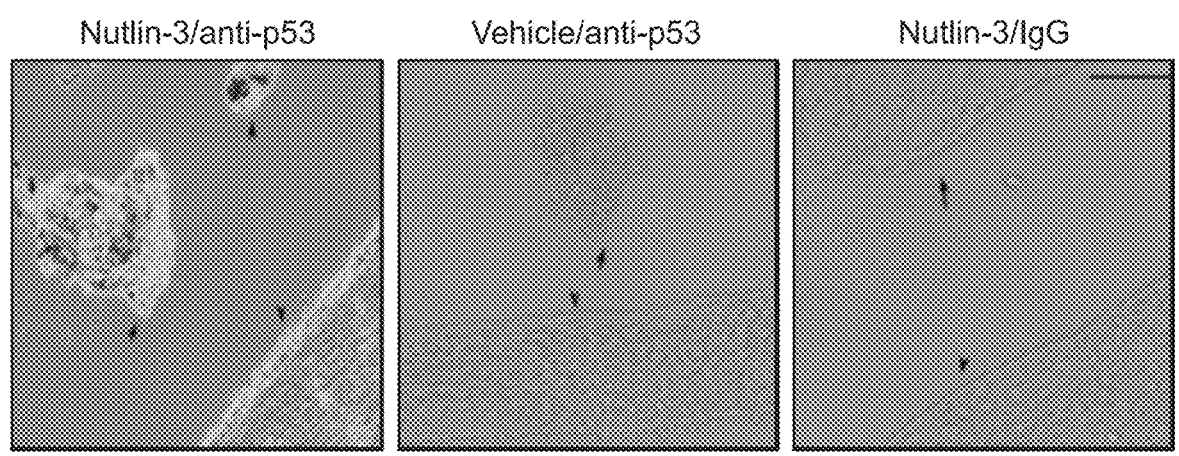

As shown in FIGS. 2A-2B, 100% of the animals in both control groups (uninjected, empty circles; or injected with vehicle, filled circles) developed complete retinal detachment (stage 5) by day 28. In contrast, 0% of the Nutlin-3a-treated animals (squares in FIG. 2A) succumbed to even partial retinal detachment (stage 3 or 4), although they did form membranes (stage 1 and 2 in FIG. 2A; FIGS. 9A-9B). Importantly, the p53 level was higher in epiretinal membranes isolated from Nutlin-3a-injected animals as compared with vehicle-injected controls (FIG. 2B). These observations indicate that Nutlin-3a treatment maintained a high level of p53 expression in cells of the epiretinal membrane and prevented retinal detachment.

Figure 3A:
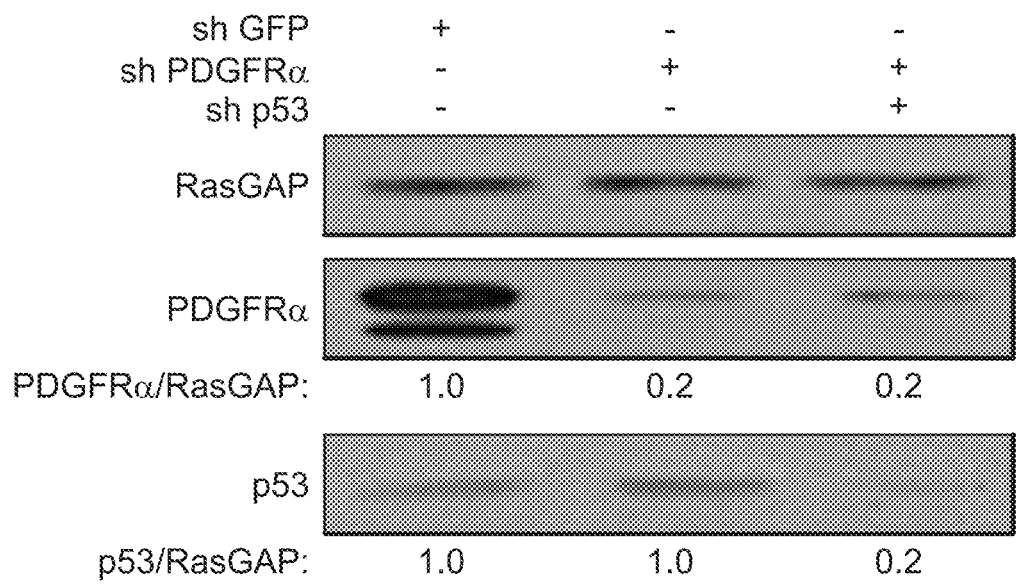
FIGS. 3A-3C include a series of western blots and photographs showing that molecularly suppressing expression of p53 rescued the ability of PDGFRα-deficient cells to contract.
Figure 3B:
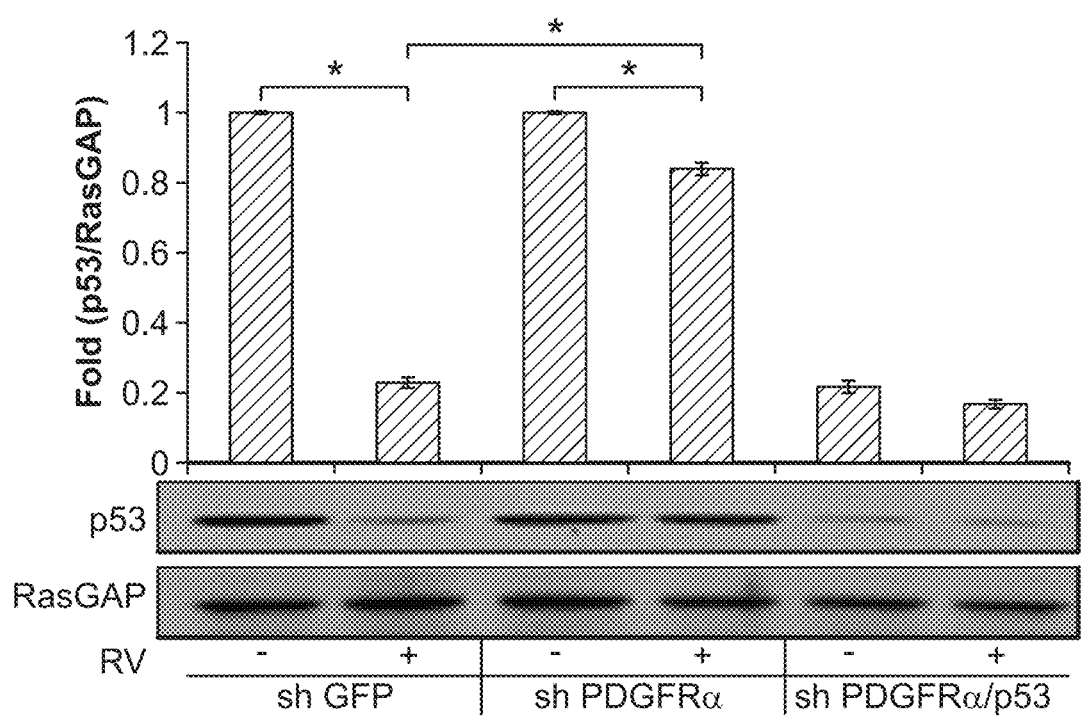
Figure 3C:
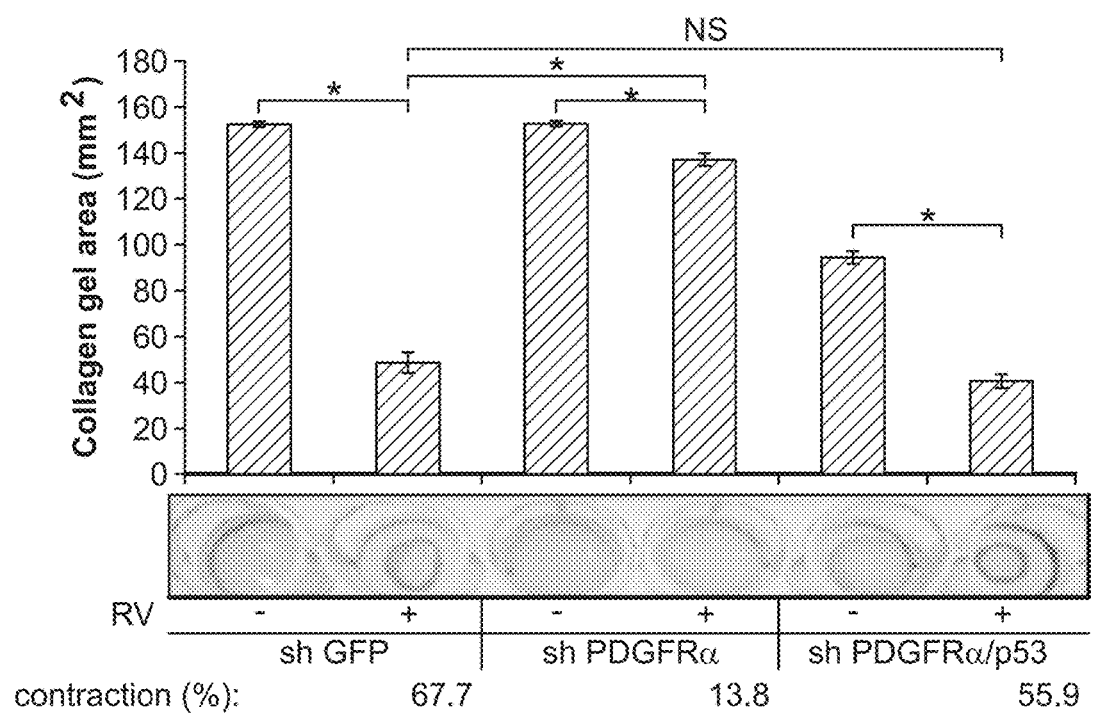

A molecular approach to assess the importance of reducing p53 for RV-mediated contraction and retinal detachment led to a similar conclusion. The overall strategy of this second approach was to reduce the PVR potential of RCFs by silencing expressing of PDGFRα, and then to test if it could be rescued by silencing expression of p53. Lentiviral-mediated delivery of shRNAs directed toward either PDGFRα, or p53 suppressed expression by at least 80% (FIG. 3A). As shown in FIG. 3B, RV-mediated suppression of p53 in sh PDGFRα cells was substantially reduced, although not completely eliminated. Similarly, RV-induced contraction of cells was largely, although not completely diminished in sh PDGFRα cells (FIG. 3C).

Figure 10A:
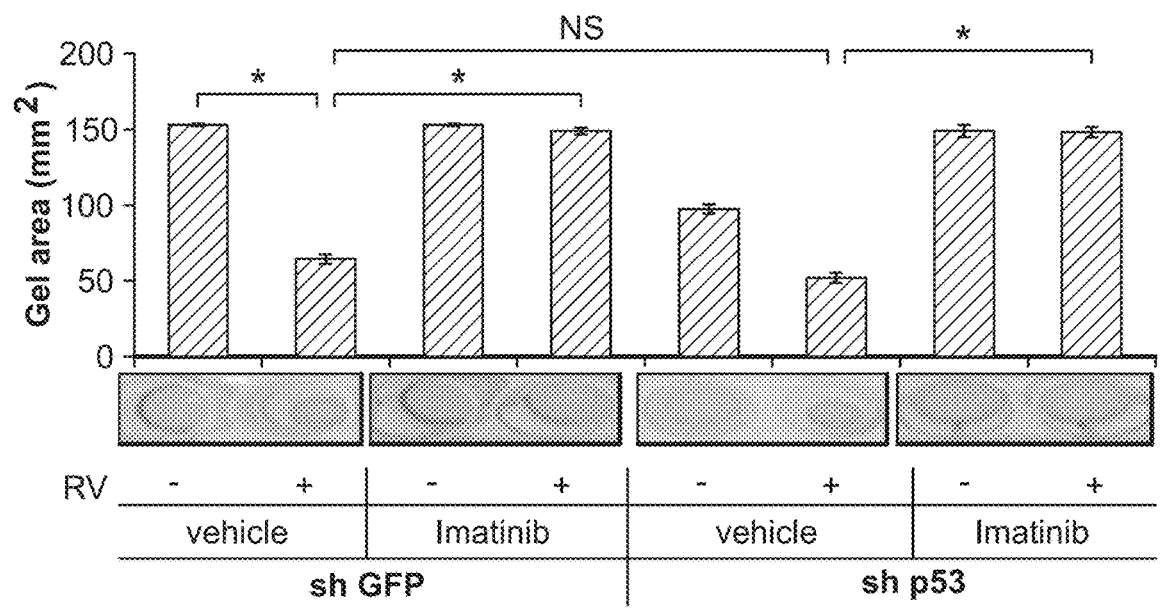
FIGS. 10A-10B include a series of bar graphs showing that inhibiting PDGFRα kinase activity blocked RV-induced collagen contraction. The indicated RCFs (50,000 cells/ml) (FIG. 10A) or F cells (1 million cells/ml) (FIG. 10B) were subjected to a collagen contraction assays as described below. F cells were immortalized mouse embryo fibroblasts derived from PDGFR knock-out mice that do not express either of the two PDGFR genes, Fα and Fβ cells are F cells in which PDGFRα or PDGFRβ has been re-expressed. After the collagen was solidified (90 minutes), DMEM or RV (diluted 1:3 in DMEM) supplemented with Imatinib (10 μM) or its vehicle was added, and replenished every 24 hours; the experiments were terminated on day 3. The panels below the bar graphs show photographs of representative gels; the data presented are representative of 3 independent experiments. The data were subjected to a paired t test; "*" denoted a statistically significant difference.
Figure 10B:
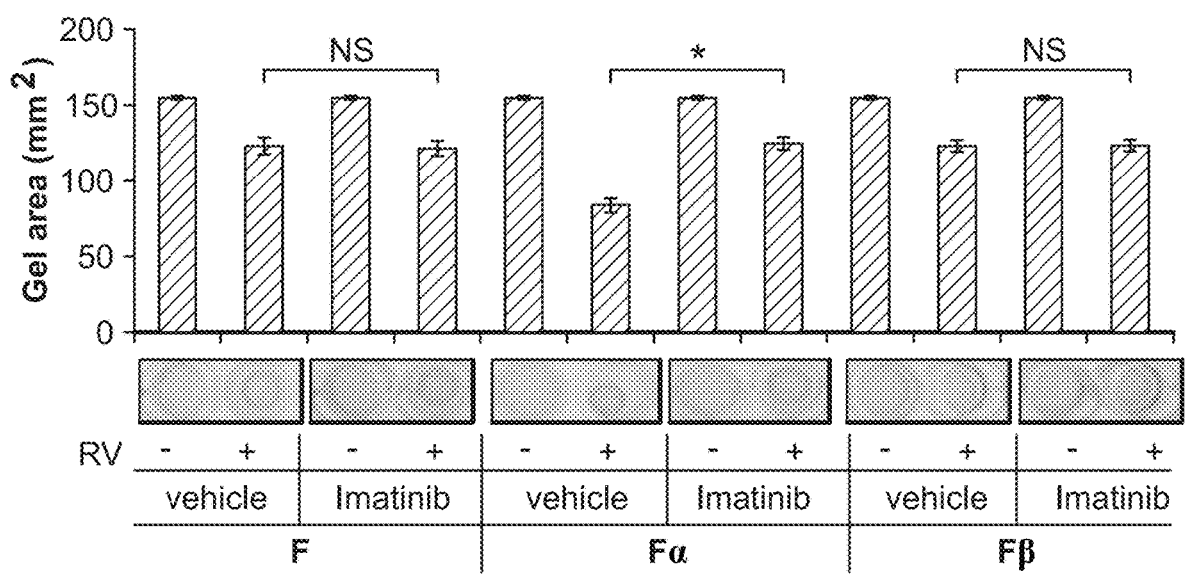

To investigate whether the incomplete suppression of RV-mediated contraction was due to the residual expression of PDGFRα, the efficacy of Imatinib to interfere with RV-induced contraction was examined. Imatinib completely blocked RV-induced contraction in sh GFP cells (FIG. 10A), which indicated that one of the Imatinib targets (abl, c-kit PDGFRα and PDGFRβ (Druker B J et al., 2001 N Engl J Med, 344:1031-1037) was essential. The previously characterized panel of cells that do or do not express PDGFRs (Andrews A et al., 1999 Invest Ophthalmol Vis Sci, 40:2683-2689) provided the opportunity to identify the relevant Imatinib target. F cells, which are immortalized fibroblasts from mice lacking both PDGFR genes (but harboring all other Imatinib targets) contracted weakly to RV, and this responses was unaffected by Imatinib (FIG. 10B). Expressing PDGFRβ in these cells did not improve RV-induced contraction or generate sensitivity to Imatinib (FIG. 10B). Finally, expression of PDGFRα improved this RV-stimulated response, which was erased by Imatinib (FIG. 10B). These observations indicate that PDGFRα was the relevant target of Imatinib, and that the modest RV-induced contraction seen in sh PDGFRα cells (FIG. 3C) was due to residual expression of PDGFRα.

Figure 4:
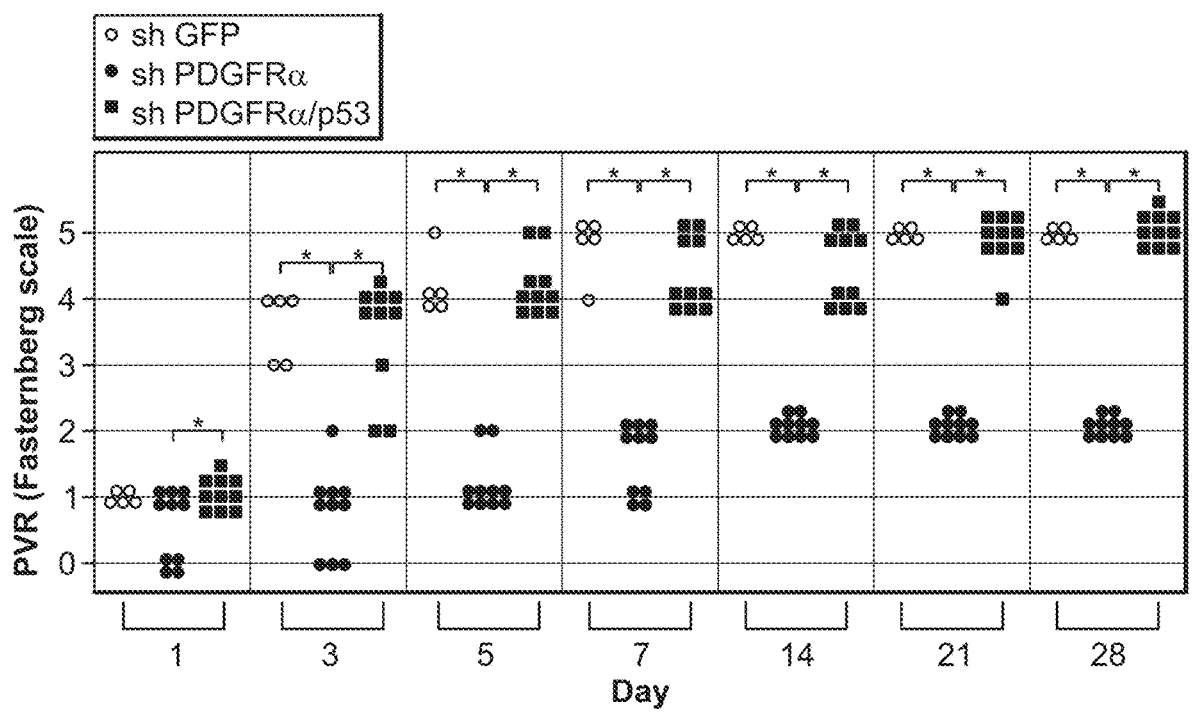
FIG. 4 is a dot plot showing that molecularly suppressing expression of p53 restored the ability of PDGFRα-deficient cells to induce retinal detachment. The cells described in FIG. 3A were compared for their PVR potential in a rabbit model of this disease. The insert indicates the type of lenti-short hairpin RNA (shRNA) used to modify the cells. PVR was induced as described below. Each symbol represents the response of an individual rabbit on the indicated day. PVR was graded according to the Fastenberg scale of classification: stage 0, no disease; stage 1, epiretinal membrane; stage 2, vitreoretinal traction without retinal detachment; stage 3, localized retinal detachment (1-2 quadrants); stage 4, extensive retinal detachment (2-4 quadrants without complete detachment); stage 5, complete retinal detachment. The data were subjected to an unpaired t test or one way ANOVA test; "*" denoted a statistically significant difference.

As expected from previous studies assessing the importance of PDGFRα for experimental PVR (Andrews A et al., 1999 Invest Ophthalmol Vis Sci, 40:2683-2689; Lei H et al, 2009 Invest Ophthalmol Vis Sci, 50:3394-3403; Ikuno Y et al., 2000 Invest Ophthalmol Vis Sci, 41:3107-3116), there was a significantly statistic reduction in the PVR potential of sh PDGFRα cells (FIG. 4). The sh PDGFRα cells failed to induce retinal detachment, although they retained their ability to form membranes, which exerted traction of the retina (FIG. 4; compare empty and filled circles). Molecularly suppressing p53 in sh PDGFRα cells fully restored their ability to induce retinal detachment (FIG. 4; compare filled circles with squares). Thus, two different experimental approaches indicated that reducing the level of p53 was essential for RV-mediated contraction and retinal detachment in an animal model of PVR.

Example 3: PDGFRα Did More than Reduce p53 to Promote Contraction

Figure 11A:
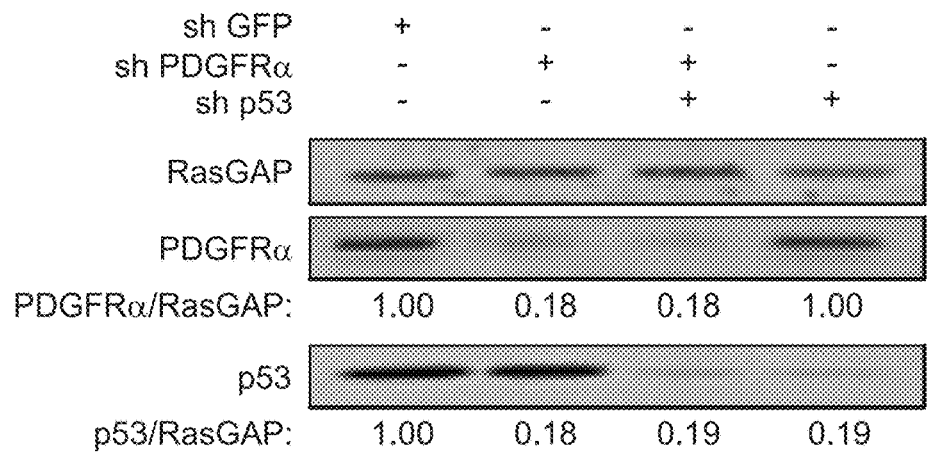
FIGS. 11A-11C include a series of photographs of western blots and bar charts showing that PDGFRα did more than suppress p53 to mediate RV-dependent contraction.
Figure 11B:
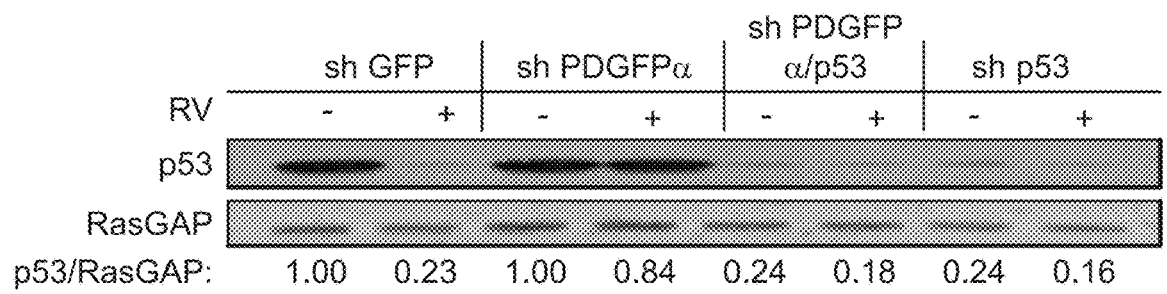
Figure 11C:
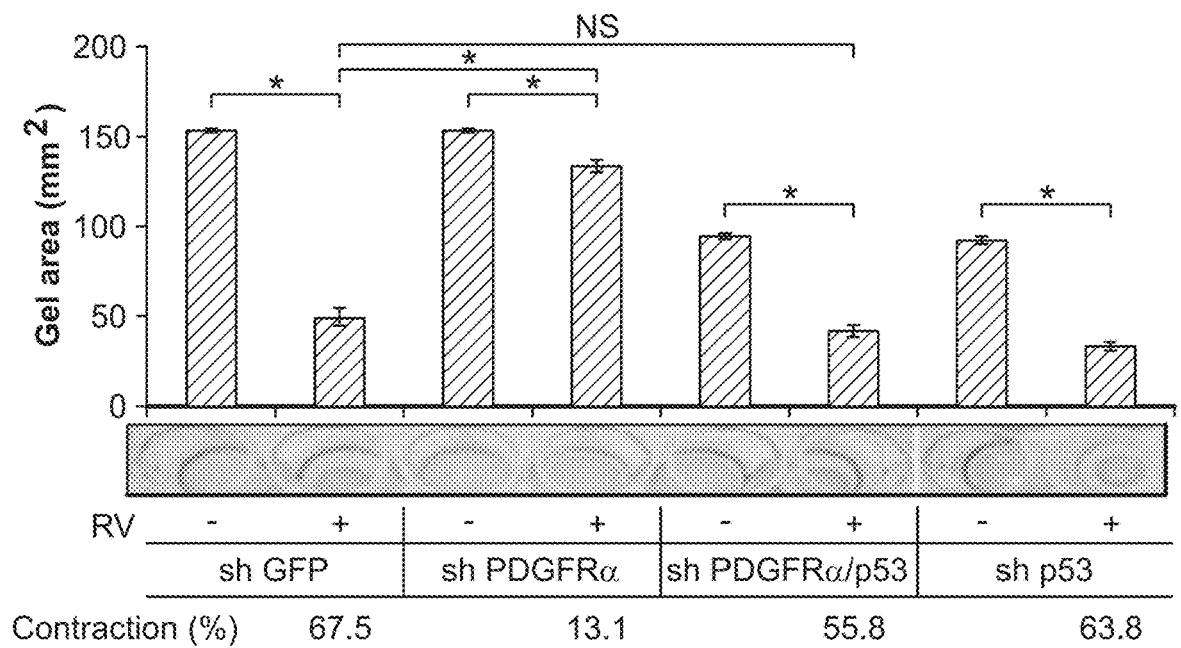
Figure 12A:
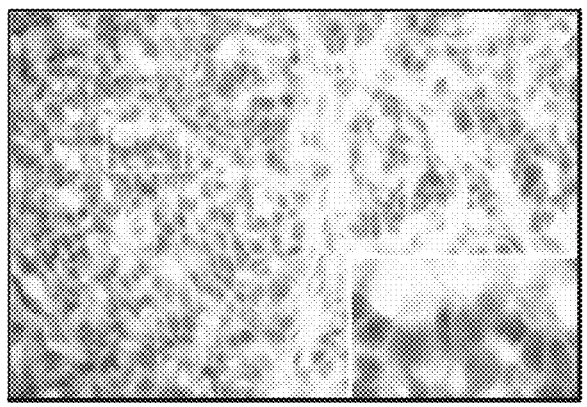
FIGS. 12A-12F include a series of photographs showing p53 was undetectable in human PVR membranes. Epiretinal membranes from patients afflicted with PVR subjected to p53 immunohistochemistry. While the positive control (rat colon cancer) demonstrated that this approach could readily detect p53 protein (FIG. 12B), p53 was undetectable in membranes from 7 different patients, three of which are shown (FIGS. 12D-12F). The green/brown pigment is routinely observed in such samples, which contain a large number of retinal pigment epithelial cells; they were also present in the section of a PVR membrane that was stained with an non-immune, isotype-matched control antibody (FIG. 12C).
Figure 12B:
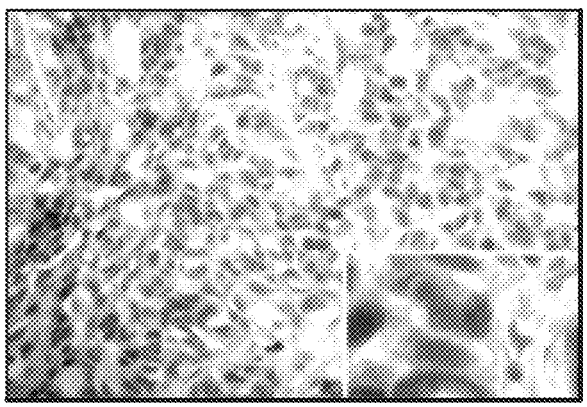
Figure 12C:
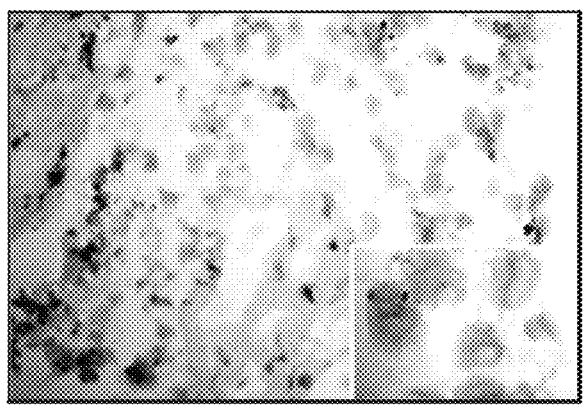
Figure 12D:
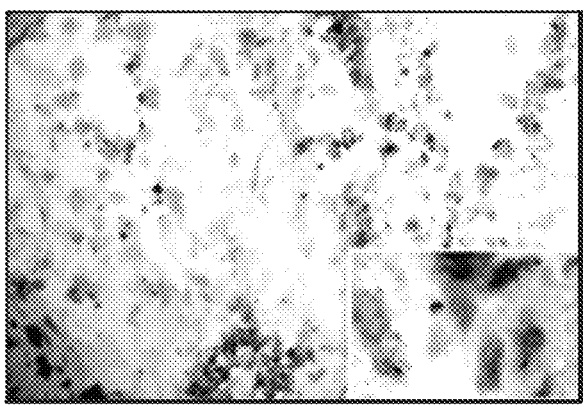
Figure 12E:
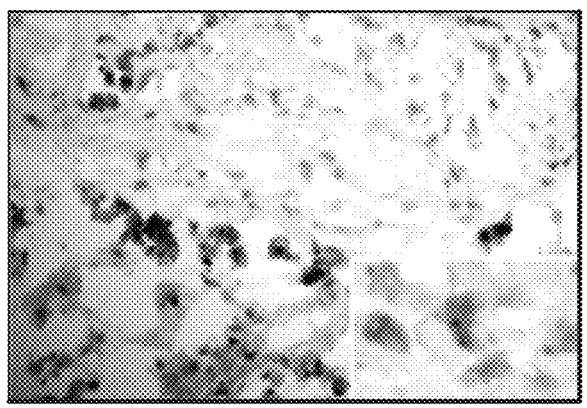
Figure 12F:
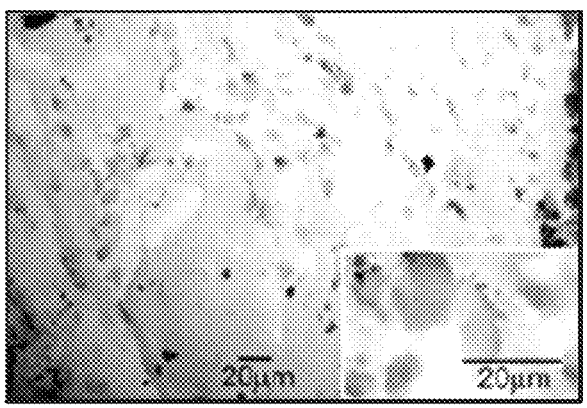

To assess if reducing p53 was the only PDGFRα-mediated event required for contraction in response to RV, this outcome was compared in sh GFP and sh p53 cells. If it was, then contraction of sh 53 cells would be RV-independent. As shown in FIGS. 11A-11C, this was not the case. While basal contraction of sh 53 cells was enhanced, they responded well to RV. These observations indicated that PDGFRα did more than reduce the level of p53 in order to mediate RV-dependent contraction.

Figure 5A:
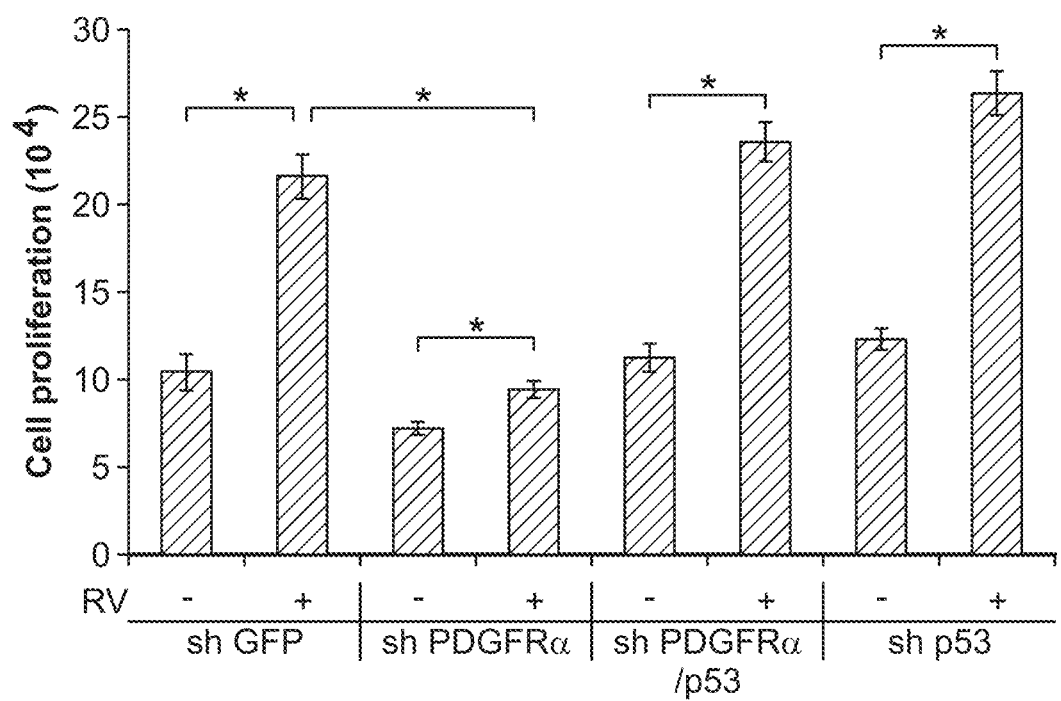
FIGS. 5A-5C include a series of bar charts demonstrating the importance of PDGFRα and suppression of p53 for RV-dependent cell proliferation and protection from apoptosis and senescence.
Figure 5B:
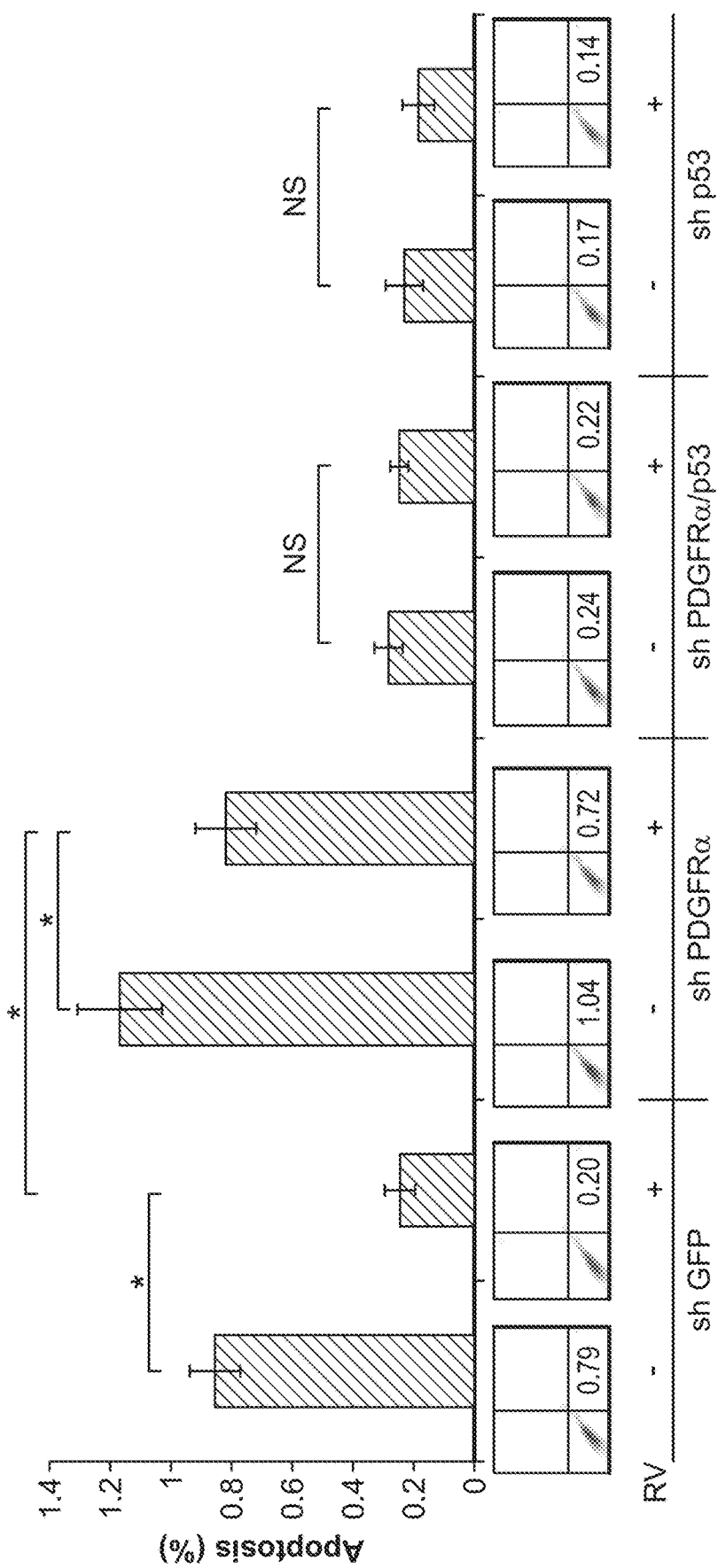
Figure 5C:
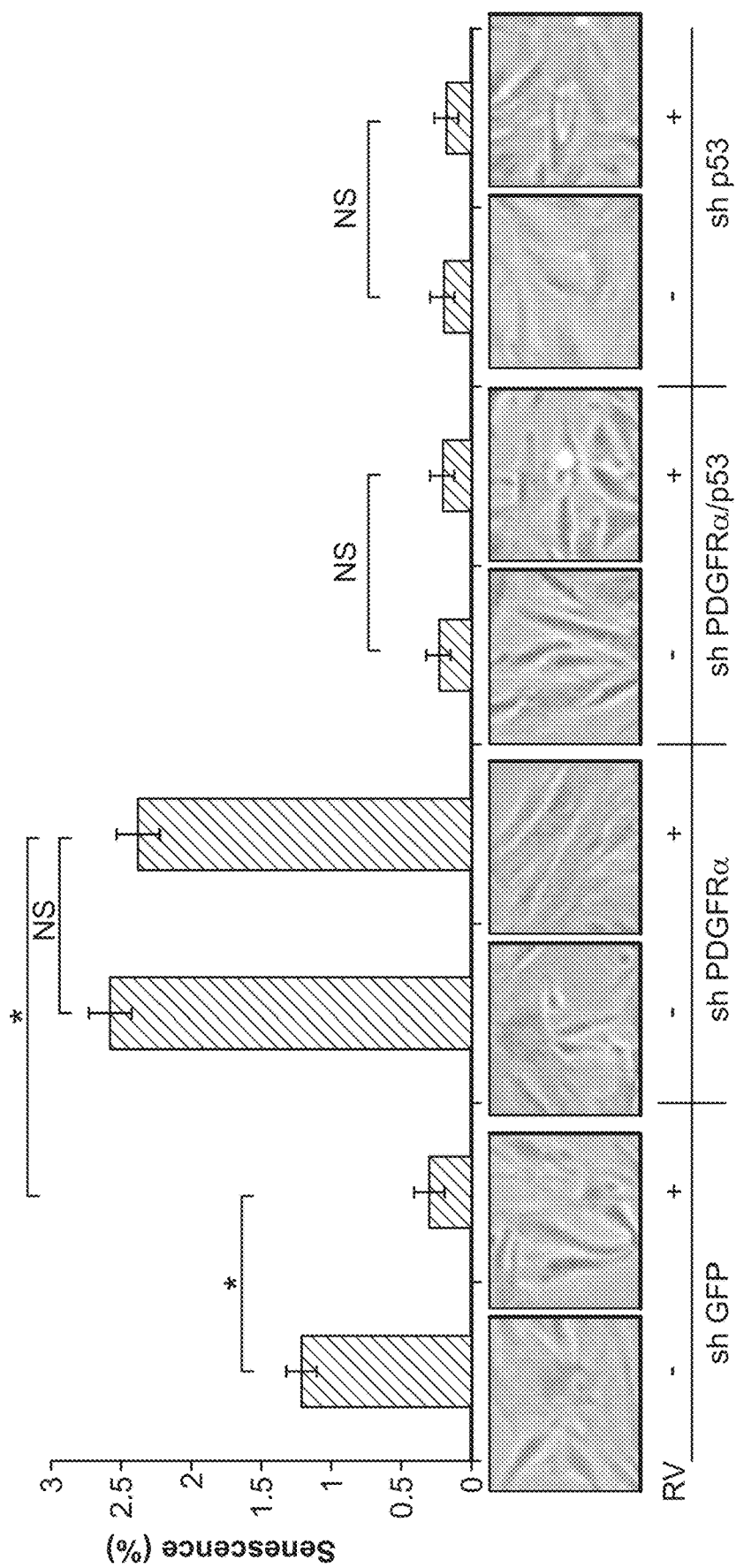

The same question was addressed for 3 additional cellular responses associated with PVR, proliferation and protection from apoptosis and senescence. Like contraction, proliferation of sh p53 cells was responsive to RV (FIG. 5A), whereas protection from apoptosis and senescence were fully engaged in unstimulated cells and RV did not enhance these responses further (FIGS. 5B and 5C). These findings indicate that reducing p53 was sufficient to trigger some of the RV-stimulated cellular responses that are associated with PVR (protection from apoptosis and senescence), whereas contraction and proliferation required an event(s) in addition to reducing the level of p53 (FIG. 6).

Residual expression of PDGFRα in shPDGFRα cells provided an opportunity to compare cellular responses associated with PVR for their dependence on the level of expression of PDGFRα. RV was unable to promote proliferation of sh PDGFRα cells or protect them from apoptosis or senescence (FIGS. 5A-5C), which indicated that these responses required expression of PDGFRα in excess of 20% of the control level. In contrast, contraction remained responsive to RV (albeit weakly) in sh PDGFRα cells (FIG. 3C). Thus, contraction required less PDGFRα expression than did proliferation or protection from apoptosis and senescence.

Example 4: Relevance to Clinical PVR

Figure 7A:
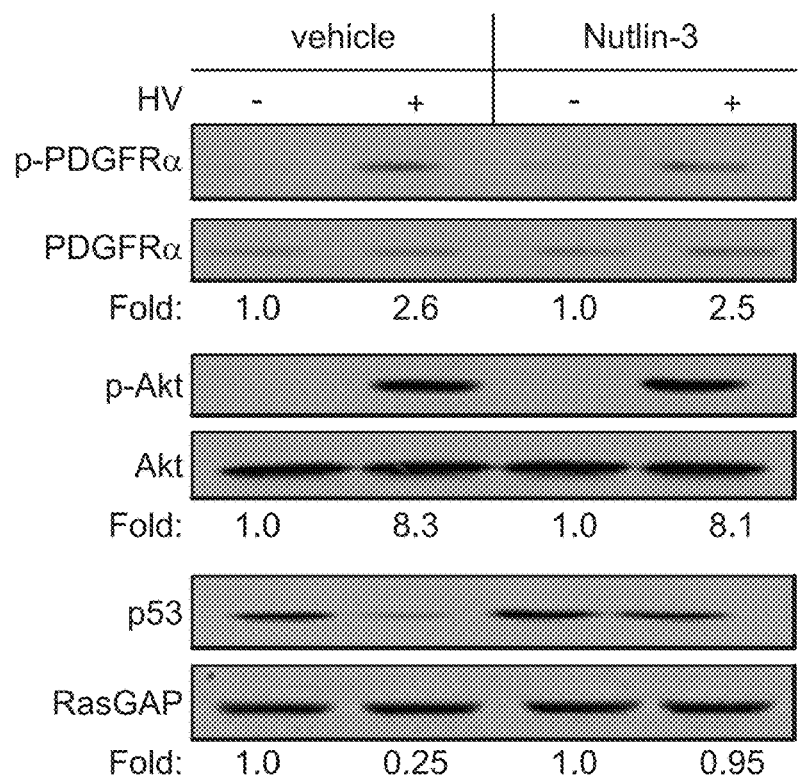
FIGS. 7A-7B include a photograph of a western blot and a bar chart showing p53 attenuated human vitreous humor (HV)-driven collagen gel contraction.
Figure 7B:
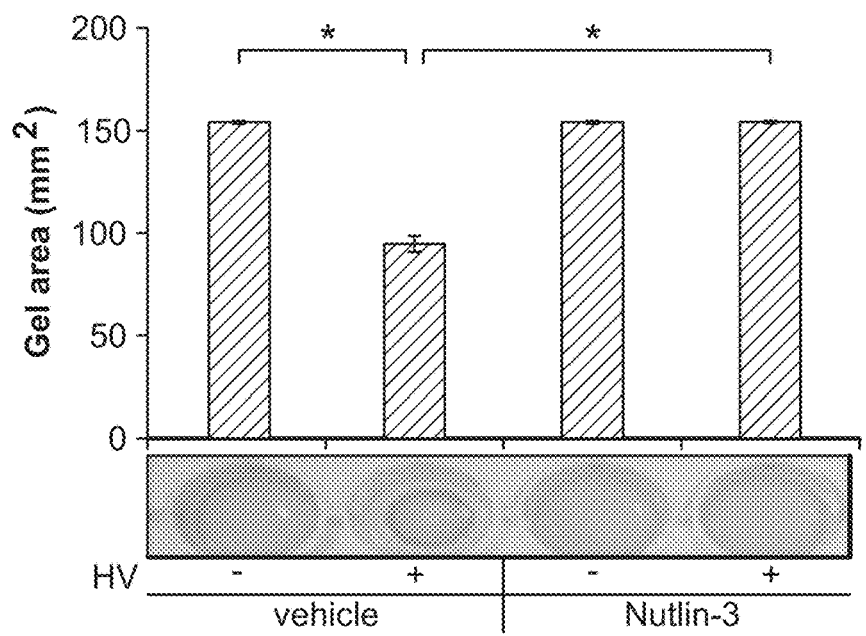

To begin to assess the clinical relevance of these findings the impact of Nutlin-3a on HV-mediated signaling events and contraction of RPE cells isolated from a human PVR membrane was considered. As shown in FIG. 7A, Nutlin-3a prevented the precipitous fall in the level of p53 observed in HV-treated control cells, without impacting upstream signaling events. Furthermore, Nutlin-3a inhibited HV-stimulated contraction of RPE-containing collagen gels (FIG. 7B). In addition, p53 was undetectable in epiretinal membranes from PVR patients (FIGS. 12A-12F). These findings indicate that Nutlin-3a had the potential to protect patients from developing PVR.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for inhibiting or reducing the severity of proliferative vitreoretinopathy (PVR) comprising:
   identifying a subject suffering from PVR; and
   contacting retinal pigment epithelial cells and/or glial cells in an eye of said subject with a composition comprising a compound comprising the chemical structure

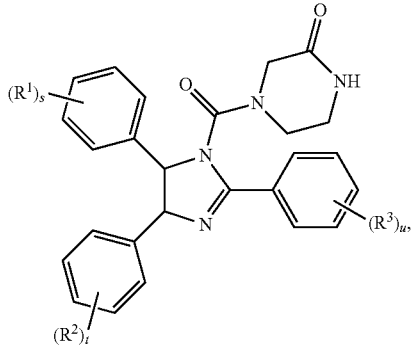

(I)

wherein
$R^1$ is independently selected from F, Cl, Br, and I;
$R^2$ is independently selected from F, Cl, Br, and I;
$R^3$ is independently selected from hydrogen, $C_1$-$C_6$ alkyl, and $C_1$-$C_6$-alkoxy;
s is 0, 1, 2, 3, 4, or 5;
t is 0, 1, 2, 3, 4, or 5; and
u is 0, 1, 2, 3, 4, or 5;
or a pharmaceutically acceptable salt thereof,
   in a sufficient amount that reduces the intra-ocular reduction of the level of p53 or that prevents p53 from interacting with human double min 2 (Hdm2), thereby inhibiting or reducing the severity of PVR.

2. The method of claim 1, wherein $R^1$ is Cl.

3. The method of claim 1, wherein said Nutlin-3a is administered at a concentration of 0.1 µM, 0.5 µM, 1.0 µM, 2.0 µM, 5 µM, 10 µM, 20 µM, 30 µM, or 50 µM.

4. The method of claim 1, wherein said Nutlin-3a is present in a concentration of 0.1-10% (mg/ml).

5. The method of claim 1, wherein said composition is administered locally to the eye using eye drops.

6. The method of claim 1, wherein said composition is administered intravitreally or subconjunctivally.

7. The method of claim 1, wherein said subject suffering from PVR has undergone rhegmatogenous retinal detachment surgery.

8. The method of claim 1, wherein the subject is older than 24 months of age.

9. The method of claim 1, wherein said composition prevents retinal detachment in said subject.

10. The method of claim 1, wherein said composition reduces the formation of epiretinal membranes in said subject.

11. The method of claim 1, wherein said composition inhibits the contraction of retinal pigment epithelial (RPE) cells in said subject.

12. The method of claim 1, wherein said composition is administered every 48 hours, every 24 hours, every 12 hours, or every 6 hours.

13. The method of claim 1, wherein said composition is administered for 1 day, 3 days, 7 days, 14 days, 30 days, 60 days, 90 days, 120 days, or 365 days.

14. The method of claim 1, wherein said composition further comprises a pharmaceutically acceptable carrier.

15. The method of claim 1, wherein the form of said composition is a solid, a paste, an ointment, a gel, a liquid, an eye drop, an aerosol, a mist, a polymer, a film, an emulsion, or a suspension.

16. The method of claim 1, wherein said subject is a human.

17. The method of claim 1, wherein said subject has not been diagnosed with a retinoblastoma.

* * * * *